United States Patent [19]

Tang et al.

[11] Patent Number: 5,075,327

[45] Date of Patent: * Dec. 24, 1991

[54] ANTIPSORIATIC AGENTS

[75] Inventors: Peng C. Tang, Bloomfield; Milan R. Uskokovic, Upper Montclair, both of N.J.

[73] Assignee: Hoffmann-La Roche Inc., Nutley, N.J.

[*] Notice: The portion of the term of this patent subsequent to Dec. 17, 2008 has been disclaimed.

[21] Appl. No.: 270,991

[22] Filed: Nov. 14, 1988

Related U.S. Application Data

[63] Continuation-in-part of Ser. No. 230,637, Aug. 10, 1988, abandoned.

[51] Int. Cl.$^5$ .................... A61K 31/35; C07D 309/30
[52] U.S. Cl. ................... 514/460; 514/863; 549/292
[58] Field of Search ............... 514/863, 460; 549/292

[56] References Cited

U.S. PATENT DOCUMENTS

| | | | |
|---|---|---|---|
| 4,231,938 | 11/1980 | Monaghan et al. | 549/292 |
| 4,293,496 | 10/1981 | Willard | 549/292 |
| 4,294,926 | 10/1981 | Monaghan et al. | 435/125 |
| 4,346,227 | 8/1982 | Terahara et al. | 560/119 |
| 4,444,784 | 4/1984 | Hoffman et al. | 549/292 |
| 4,450,171 | 5/1984 | Hoffman et al. | 549/292 |
| 4,582,915 | 4/1986 | Sleteinger et al. | 549/292 |
| 4,611,067 | 9/1986 | Valente et al. | 549/419 |
| 4,668,699 | 5/1987 | Hoffman et al. | 549/292 |
| 4,766,145 | 8/1988 | Lee et al. | 514/460 |
| 4,771,071 | 9/1988 | Hoffman et al. | 514/460 |
| 4,795,811 | 1/1989 | Graham et al. | 544/6 |

FOREIGN PATENT DOCUMENTS

| | | |
|---|---|---|
| 245004 | 11/1987 | European Pat. Off. |
| 122483 | 7/1984 | Japan . |
| 2073193 | 10/1981 | United Kingdom . |

OTHER PUBLICATIONS

Ponec et al., "Differentiation of Human Keratinocytes: Changes in Lipid Synthesis, Plasma Membrane Lipid Composition and $^{125}$I-EGF Binding Upon Administration of 25-Hydroxy Cholesterol and Meloinolin" J. Cellular Physiology, 133:358-364, (1987).
J. Antibiot. 36(5), 604 (1983).
J. Antibiot. 36(5), 608 (1983).
J. Antibiot., 36(7), 918 (1983).
J. Med. Chem., 28(4) 401 (1985).
J. Antibiot., 38(5), 605 (1985).
Chemical Abstract 102:7864 3F (1985).
Page 96 of the Chemical and Engineering News, Aug. 1, 1988.
Chem. Abstract 180 "Total Synthesis of the Angular Methyl Regioisomer of Compactin".
Drugs of Future, vol. 13, No. 5, 1988, p. 475.
Clin. Pharm., 7/1, 21-36 (1988).
J. Cell Physiol., 133/2, 358-364 (1987).

Fitzpatrick, T. B. et al., Dermatology in General Medicine, 3rd Ed., Chapter 5, pp. 49-50 and 154-159 (1987).

Primary Examiner—C. Warren Ivy
Assistant Examiner—Amelia A. Owens
Attorney, Agent, or Firm—George M. Gould; George W. Johnston; Alan P. Kass

[57] ABSTRACT

A compound and process of making thereof of formula

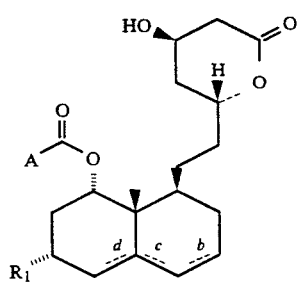

wherein $R_1$ is hydrogen; and A is alkyl; cycloalkyl; alkenyl; alkyl substituted with trifluoromethyl; phenyl; halophenyl; phenyl-$C_{1-3}$ alkyl; phenyl-$C_{1-3}$ alkyl substituted on the phenyl with 1 to 3 substituents selected from the group consisting of halo, $C_{1-3}$ alkyl, and $C_{1-3}$ alkoxy; or A is

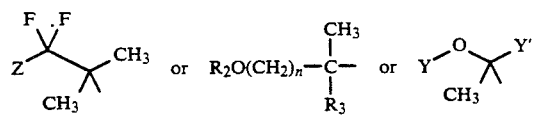

wherein Z is lower alkyl; $R_2$ is hydrogen or

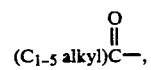

$R_3$ is hydrogen or methyl, and n is 1 to 5; Y is phenyl, is phenyl substituted by 1 to 3 substituents selected from the group consisting of halo, lower alkyl, and lower alkoxy; Y' is hydrogen or methyl; and b and d are carbon-carbon bonds or c is a carbon-carbon bond;

or the corresponding hydroxy acid of formula (Abstract continued on next page.)

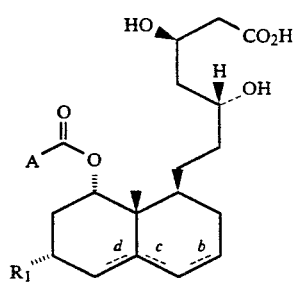

II  wherein A, and $R_1$, $R_2$, $R_3$, Y and Y' are as described above, or a pharmaceutically acceptable salt of said acid, an alkyl ester of said acid, an acetylamino-substituted-$C_{1-4}$ alkyl ester of said acid, a phenyl-dimethylamino ester of said acid or a α-monoglyceride of said acid, and b and d are carbon-carbon bonds or c is a carbon-carbon bond.

The compound of formula I and II are useful in treating hyperproliferative skin diseases, such as psoriasis.

8 Claims, No Drawings

ANTIPSORIATIC AGENTS

CROSS REFERENCE TO RELATED APPLICATIONS

This is a continuation in part of U.S. application Ser. No. 230,637 filed Aug. 10, 1988, now abandoned.

BACKGROUND OF THE INVENTION

Natural occurring compounds known as mevinolin and its derivatives inhibit the biosynthesis of cholesterol and thus are useful for their antihypercholesterolemic activity. (See U.S. Pat. No. 4,444,784 issued to Hoffman et al on Apr. 24, 1984 and U.S. Pat. No. 4,450,171 issued to Hoffman et al on May 22, 1984). The mevinolin compounds are isolated from the microfungus of the genus Aspergillus as described in U.S. Pat. Nos. 4,231,938 issued to Monaghan et al on Nov. 4, 1980 and U.S. Pat. No. 4,294,926 issued to Monaghan et al on Oct. 13, 1981.

The most active member of this group of natural compounds in inhibiting cholesterol biosynthesis is mevinolin. (See U.S. Pat. No. 4,450,171, col. 1, lines 43–51).

As antihypercholesterolemic agents, these known compounds may be administered orally or parenterally, although the oral route is generally desirable. Moreover, these compounds have been found to be useful as anti-fungal agents which may be sprayed or dusted onto plants to be protected (See U.S. Pat. No. 4,450,171; col. 12, lines 45–66).

A difference between all of the known compounds disclosed in the above patents, and the compounds of the invention, is that the compounds of the invention possess a β-methyl in the 8a-position.

BRIEF SUMMARY OF THE INVENTION

The invention relates to compounds, process of making the compounds and method of using the compounds to treat hyperproliferative skin diseases, such as, psoriasis, having the formula

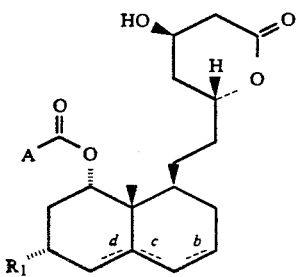

wherein $R_1$ is hydrogen; and A is alkyl; cycloalkyl; alkenyl; alkyl substituted with trifluoromethyl; phenyl; halophenyl; phenyl-$C_{1-3}$ alkyl; phenyl-$C_{1-3}$ alkyl substituted on the phenyl with 1 to 3 substituents selected from the group consisting of halo, $C_{1-3}$ alkyl, and $C_{1-3}$ alkoxy; or A is

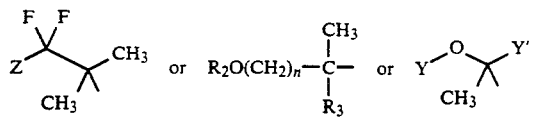

wherein Z is lower alkyl; $R_2$ is hydrogen or

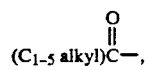

$R_3$ is hydrogen or methyl, and n is 1 to 5; Y is phenyl, or phenyl substituted by 1 to 3 substituents selected from the group consisting of halo, lower alkyl, and lower alkoxy; Y' is hydrogen or methyl; and b and d are carbon-carbon bonds or c is a carbon-carbon bond;

or the corresponding hydroxy acid of formula

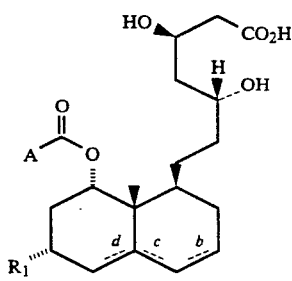

wherein A and $R_1$ are as described above, or a pharmaceutically acceptable salt of said acid, an alkyl ester of said acid, an acetylamino-substituted-$C_{1-4}$ alkyl ester of said acid, a phenyl-dimethylamino ester of said acid or a α-monoglyceride of said acid, and b and d are carbon-carbon bonds or c is a carbon-carbon bond.

It has been unexpectedly found that compounds of formulas I and II are useful in the treatment of hyperproliferative skin diseases, such as psoriasis, basal cell carcinomas, keratosis, and disorders of keratinization. These compounds may be administered either orally or topically to psoriatic skin.

DETAILED DESCRIPTION OF THE INVENTION

The invention relates to compounds, processes of making the compounds and methods of using the compounds to treat hyperproliferative skin diseases, such as, psoriasis, having the formula

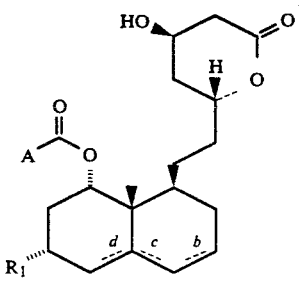

wherein $R_1$ is hydrogen; and A is alkyl; cycloalkyl; alkenyl; alkyl substituted with trifluoromethyl;

phenyl; halophenyl; phenyl-$C_{1-3}$ alkyl; phenyl-$C_{1-3}$ alkyl substituted on the phenyl with 1 to 3 substituents selected from the group consisting of halo, $C_{1-3}$ alkyl, and $C_{1-3}$ alkoxy; or A is

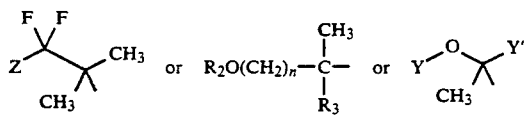

wherein Z is lower alkyl; $R_2$ is hydrogen or

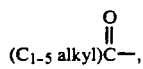

$R_3$ is hydrogen or methyl, and n is 1 to 5; Y is phenyl, or phenyl substituted by 1 to 3 substituents selected from the group consisting of halo, lower alkyl, and lower alkoxy; Y' is hydrogen or methyl; and b and d are carbon-carbon bonds or c is a carbon-carbon bond;

or the corresponding hydroxy acid of formula

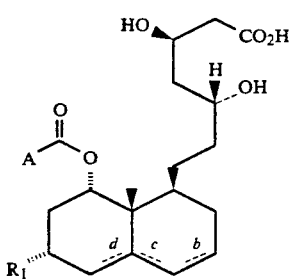

wherein A and $R_1$ are as described above, or a pharmaceutically acceptable salt of said acid, an alkyl ester of said acid, an acetylamino-substituted-$C_{1-4}$ alkyl ester of said acid, a phenyl-dimethylamino ester of said acid or a α-monoglyceride of said acid and b and d are carbon-carbon bonds or c is a carbon-carbon bond.

Compounds of formulas I and II are also useful in lowering cholesterol.

"Normal skin" refers to skin which undergoes a sequence of changes resulting from changes in the proliferative basal cells to the formation of terminally differentiated corneocytes. As the epidermis differentiates in the skin, keratinocytes undergo a destructive process of terminal differentiation to produce a cellular protective layer of the stratum corneum. The process begins with the basal layer of cells proliferating and entering into the spinous layer of the skin. Within the spinous layer there is increased metabolic activity with a concomitant increase in the precursor protein for the cornified envelope and changes in the keratin expression. As the cells pass higher up the skin into the stratum corneum, enzymes responsible for crosslinking envelope proteins are active, profilaggrin processing is initiated, and higher molecular weight keratins appear. As the cell passes into the stratum corneum it is converted into a keratin filled, cornified envelope without nucleus or other organelles.

As used herein, the term "psoriasis" refers to a hyperproliferative skin disease which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer causing an increase in the basal cell cycle. Additionally, hyperkeratotic and parakeratotic cells are present.

The terms "keratosis", "basal cell carcinomas" and "disorders of keratinization" refers to hyperproliferative skin diseases in which the regulatory mechanisms for the proliferation and differentiation of skin cells are disrupted.

The compounds of formula I or II are active as skin hyperproliferation antagonists, that is, as agents which inhibit the hyperproliferation of keratinocytes. The compounds further antagonize alterations in the differentiation of keratinocytes. Accordingly, the compounds are useful as agents for the treatment of hyperproliferative skin diseases such as psoriasis, basal cell carcinomas, disorders of keratinization and keratosis.

In the formulas presented herein, the various substituents are illustrated as joined to the nucleus by one of the following notations: a wedged solid line (◄━) indicates a substituent which is above the plane of the molecule (β-orientation), a wedged dotted line (ıııııııı) indicates a substituent which is below the plane of the molecule (α-orientation) and a wavy line (∧∧) indicates a substituent which may be either above or below the plane of the molecule.

As used herein the term "halo" means chloro, fluoro, bromo or iodo.

As used herein, the term "alkyl" denotes a straight or branched-chain alkyl group containing 1 to 10 carbon atoms, for example, methyl, ethyl, propyl, isopropyl, butyl, t-butyl and the like. The term "lower alkyl" denotes alkyl as above having 1 to 6 carbon atoms.

The term "cycloalkyl" denotes a cycloalkyl having 3 to 10 carbon atoms such as cyclopropyl, cyclobutyl, and the like.

The term "alkenyl" denotes a straight or branched chain alkenyl having 2 to 10 carbon atoms such as ethenyl, propenyl and the like.

The term "alkyl substituted with trifluoromethyl" denotes a $C_{1-10}$ straight or branched chain alkyl having one hydrogen replaced by trifluoromethyl.

The term "halophenyl" denotes a phenyl substituted with up to three halogens.

The term "phenyl-$C_{1-3}$ alkyl" denotes an alkyl having 1-3 carbon atoms and one of whose hydrogens is replaced by a phenyl.

The term "lower alkoxy" refers to straight or branched chain alkoxy group containing 1-10 carbon atoms, for example, ethoxy, ethoxy, propoxy and the like.

The invention relates to compounds, process of making the compounds and method of using the compounds to treat hyperproliferative skin diseases, such as, psoriasis, having the formula I.

A preferred group of compounds of formula I are those wherein $R_1$ is lower alkyl.

Preferred compounds of the invention are:

[4R-[4β,6β,6[8S(8β,8aβ]]]-6-[2-[1,2,6,7,8,8a-hexahydro-8-(2,2-dimethyl-1-oxobutoxy)-8a-methyl-1-naphthalenyl]ethyl]tetrahydro-4-hydroxy-2H-pyran-2-one; and

[4R-(4α,6β),6[1S-[1α,8β(S),8aα]]]-6-[2-[[1,2,6,7,8,8a-hexahydro-8a-methyl-8-(2methyl-1-oxobutoxy)-1-naphthalenyl]ethyl]tetrahydro-4-hydroxy-2H-pyran-2-one.

The invention also relates to intermediates of the formula

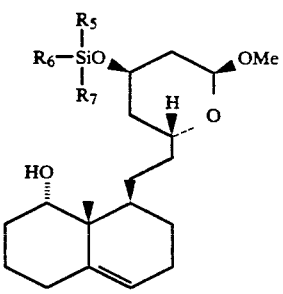

VI wherein R$_5$, R$_6$ and R$_7$ are independently lower alkyl or phenyl with the proviso that no more than two of R$_5$, R$_6$ and R$_7$ are phenyl.

The invention also relates to intermediates of the formula

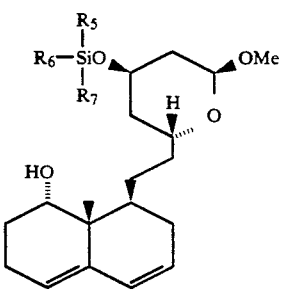

X wherein R$_5$, R$_6$ and R$_7$ are independently lower alkyl or phenyl with the proviso that no more than two of R$_5$, R$_6$ and R$_7$ are phenyl.

Another aspect of the invention is the compound, [1S-(1α,8β,8aβ)]-8-(2-formylethyl)-8a-methyl-1,2,3,4,6,7,8,8a-octahydro-1-naphthalenol-acetate as described in Example 13 below and is active as an agent in the treatment of hyperproliferative skin diseases and as an agent in lowering cholesterol.

In accordance with the invention, the compounds of formula I can be prepared as hereinafter described in Reaction Schemes I-III.

REACTION SCHEME I

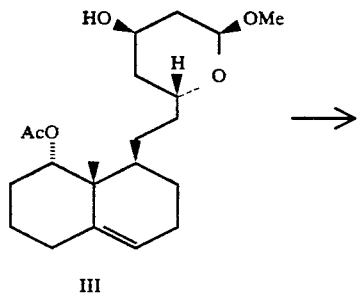

III

-continued
REACTION SCHEME I

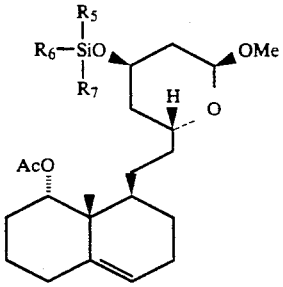

IV

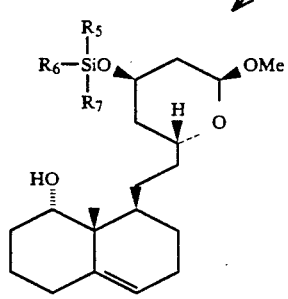

VI wherein R$_5$, R$_6$ and R$_7$ are independently lower alkyl or phenyl with he proviso that no more than two of R$_5$, R$_6$ and R$_7$ are phenyl.

The starting material in Reaction Scheme I is described hereafter.

As shown in Reaction Scheme I above, the compound of formula III is treated with a compound for forming protecting groups such as t-butyldiphenylchlorosilane, chlorotriethylsilane, or more preferably t-butylchlorodimethylsilane in a polar, aprotic or alkyl halide solvent such as N,N-dimethylacetamide, dichloromethane, or more preferably N,N-dimethylformamide at about 50° C. to about 80° C. preferably about 60° C., to obtain a compound of formula

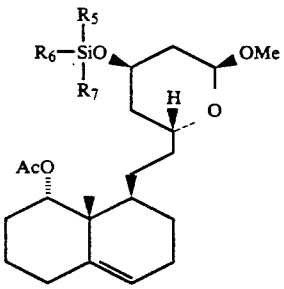

IV wherein R$_5$, R$_6$ and R$_7$ are as described above upon conventional work-up.

The compound for forming protecting groups is a compound of formula

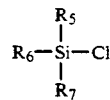

V wherein $R_5$, $R_6$ and $R_7$ are as described above which is known or can be prepared in accordance with known means.

The compound of formula V is reacted with a cleaving reagent such as lithium aluminum hydride, sodium hydroxide, or more preferably diisobutyl aluminum hydride in an ether solvent such as a mixture of diethyl ether and tetrahydrofuran at a temperature in the range of about $-85°$ C. to about $-30°$ C. preferably at about $-78°$ C. to achieve upon conventional work-up an alcohol of the formula

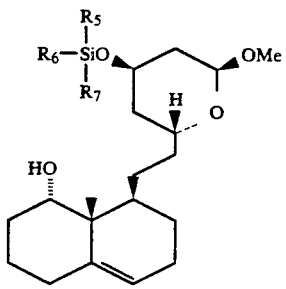

VI wherein $R_5$, $R_6$ and $R_7$ are as described above.

ride, in the presence of a buffer such as sodium carbonate at about $-10°$ C. to about $10°$ C., preferably $0°$ C.

The reaction is quenched with a reducing agent such as triphenylphosphine or dimethylsulfide, and upon conventional work-up there is obtained a compound of the formula

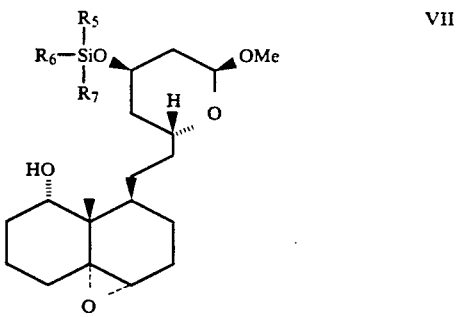

VII wherein $R_5$, $R_6$ and $R_7$ are as described above.

This α-epoxide is a part of a 30:1 separable mixture of α- and β-epoxides. The α-epoxide of the compound of formula VII may optionally be separated out for further reaction in this reaction scheme.

REACTION SCHEME II

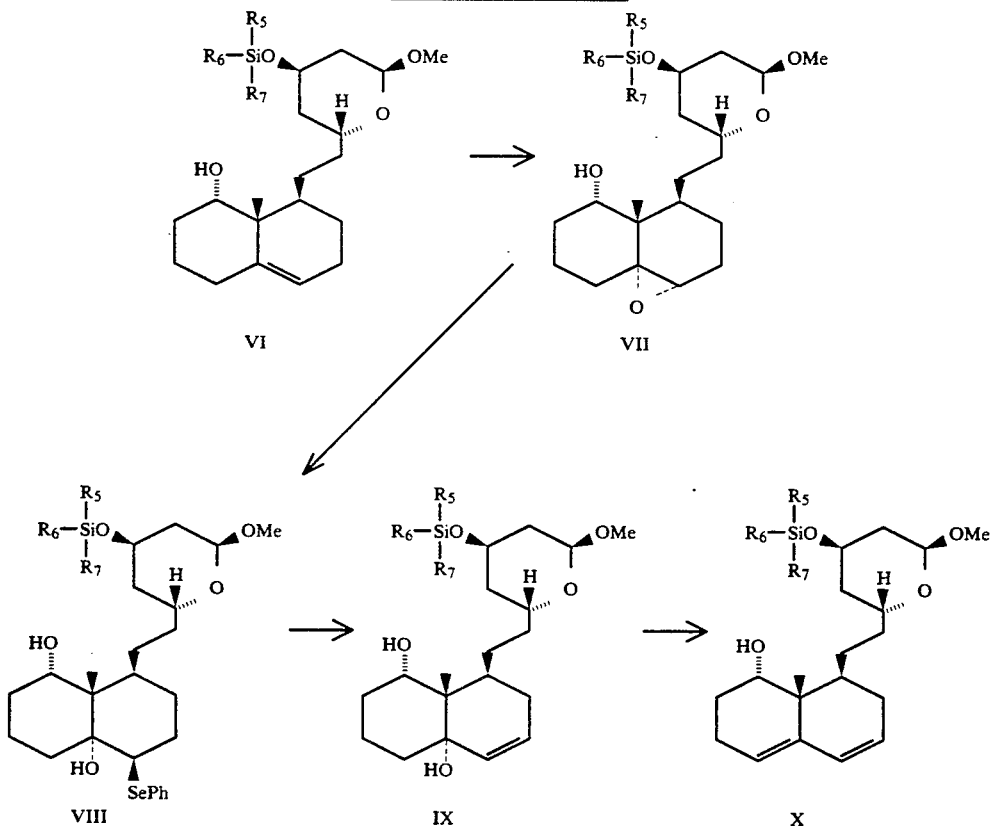

wherein $R_5$, $R_6$ and $R_7$ are as described above.

As shown in Reaction Scheme 2 above, the compound of formula VI is then epoxidized stereoselectively by a reagent such as peracetic acid, trifluoroperacetic acid, or more preferably 3-chloroperbenzoic acid in a polar organic solvent such as 1,2-dichloroethane, trichloromethane, or more preferably methylene chlo- The compound of formula VII is cleaved with a nucleophile such as sodium thiophenoxide, sodium iodide, or more preferably sodium selenophenoxide which is prepared by adding sodium borohydride to a solution of diphenyldiselenide in a lower alkanolic solvent such as methanol, propanol, or more preferably ethanol. To this reagent mixture is added the compound of formula VII in a lower alkanol and the resulting reaction mixture is heated at a temperature in a range of about 70° C. to about 100° C., preferably about 90° C., to give, upon conventional work-up the diol of the formula

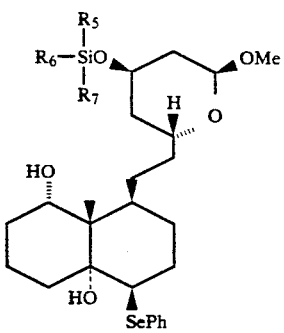   VIII wherein $R_5$, $R_6$ and $R_7$ are as described above.

The compound of formula VIII is reacted with an oxidant such as 3-chloroperbenzoic acid, sodium periodate or more preferably aqueous hydrogen peroxide in the presence of a base such as pyridine in an etheral solvent such as diethyl ether or more preferably tetrahydrofuran at about 25° C. to about 70° C., preferably about 50° C., to obtain a diol of formula

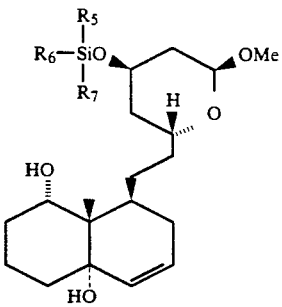   IX wherein $R_5$, $R_6$ and $R_7$ are as described above.

The diol of formula IX is treated with a dehydrating agent such as sulfuric acid, p-toluene sulfonic acid, or more preferably pyridinium p-toluenesulfonate in a polar organic solvent such as an alkyl halide, like 1,2-dichloroethane, trichloromethane, or methylene chloride, at ambient temperature to obtain, upon conventional work-up a compound of the formula

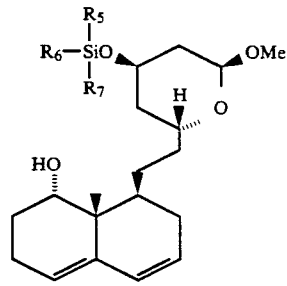   X wherein $R_5$, $R_6$ and $R_7$ are as described above.

REACTION SCHEME III

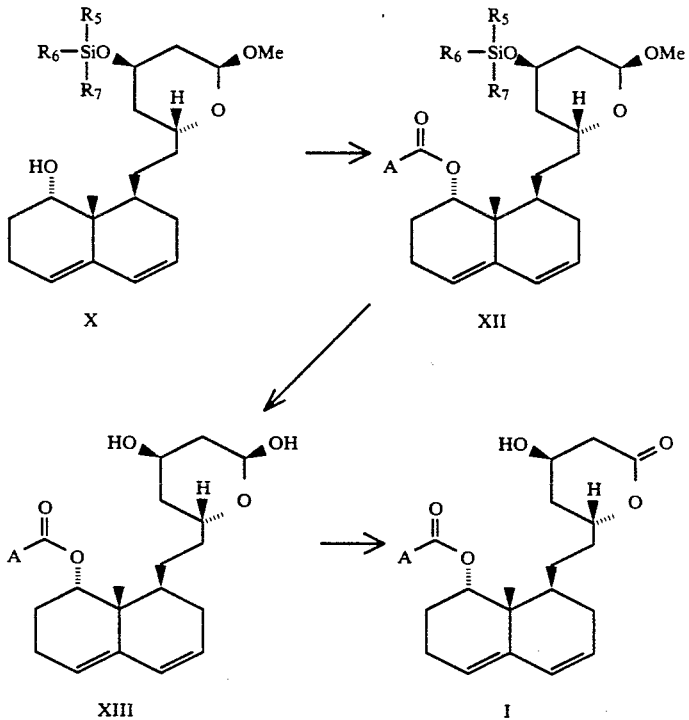

wherein $R_5$, $R_6$, $R_7$ and A are as described above.

As shown in Reaction Scheme III above, the compound of formula X may be reacted with a compound of the formula

     XI wherein A is as described above and Z is halogen, hydroxyl or

Compounds of formula XI are known or can be prepared in accordance with known methods.

As described in Reaction Scheme 3, the compound of formula X may be reacted with a compound of the formula XI to obtain a compound of formula

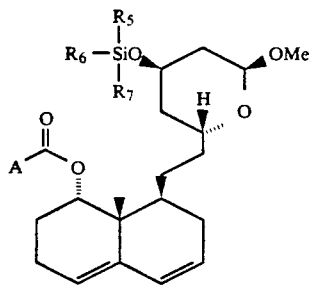    XII wherein $R_5$, $R_6$, $R_7$ and A are as described above.

The reaction is conducted in an organic solvent such as pyridine or methylene chloride in the presence of a catalyst such as 4-diethylaminopyridine, 4-dipropylaminopyridine, or more preferably 4-dimethylamino pyridine optionally in the presence of dicyclohexylcarbodiimide when a compound of formula XI wherein Z is hydroxyl is used, to yield a compound of formula XII.

The hydrolysis of the resulting compound of formula XII is accomplished by an acid such as aqueous sulfuric acid, aqueous hydrofluoric acid or aqueous hydrochloric acid in an ether or lower alkanol solvent such as methanol, ethanol or tetrahydrofuran to obtain the compound of formula

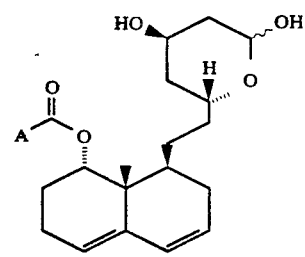    XIII wherein A is as described above, upon conventional work-up.

The compound of formula XIII is then oxidized by treatment with silver carbonate, or more preferably silver carbonate on celite in an aromatic solvent such as toluene, xylene, or more preferably benzene at a temperature between about 80° C. to about 120° C. more preferably about 95° C. to yield, upon conventional work-up the compound of formula I wherein b and d are carbon-carbon bonds.

Alternatively, a compound of formula VI may be used directly as the starting material in Reaction Scheme 3, in place of a compound of formula X, to obtain compounds of formula I wherein c is a carbon-carbon bond.

Compounds of formula I can be hydrolyzed with bases such as NaOH to yield the corresponding salts such as sodium salts. Careful acidification of the salts yields the corresponding hydroxy acid form of formula II. Compounds of formula II can conversely be converted to compounds of formula I under acidic pH conditions.

Treating compounds of formula I under acidic or basic catalysis with methanol, ethanol, propanol, or butanol or with phenyl-, dimethylamino-, or acetylamino-alkanols yields the corresponding esters of compounds of formula II in a manner analogous to those known in the art.

EFFECT OF COMPOUNDS OF FORMULAS I AND II ON THE PROLIFERATION OF CULTURED HUMAN KERATINOCYTES

The compounds of formulas I and II as described above can be administered orally, for the treatment of hyperproliferative skin diseases such as psoriasis, basal cell carcinomas, disorders of keratinization and keratosis to warm-blooded animals which need such treatment. More specifically, the compounds of formula I can be administered orally to the adult human in dosages that are in the range of about 1.0 to 200 milligrams per day and preferably about 20 to 100 milligrams per day for the treatment of hyperproliferative skin diseases such as psoriasis, basal cell carcinomas, disorders of keratinization and keratosis.

The compounds of formulas I or II as described above can be administered topically, for treatment of hyperproliferative skin diseases, such as psoriasis, basal cell carcinomas, disorders of keratinization and keratosis to warm-blooded animals which need such treatment. More specifically, the compounds of formula I as described above can be administered topically in dosages that are in 1–200 micrograms per gram of topical formulation per day for the treatment of such diseases.

The compounds of formula I and II are useful as cholesterol lowering agents and they may be administered orally for the purpose of lowering cholesterol.

The useful activity of compounds of formula I or II as agents for the treatment of hyperproliferative skin diseases are demonstrated by the following test procedures.

MATERIALS AND METHODS

1. Culture Conditions

Human neonatal foreskins were collected by circumcision and placed into tubes containing DMEM media. Upon arrival at the laboratory the foreskins were mechanically trimmed of excess dermis and treated with a solution of trypsin/EDTA (0.05%/0.02%) at 4° C. overnight. The epidermis was stripped from the dermis, agitated in buffered saline to remove basal keratinocytes and the stratum corneum buffer was removed. The separated cells were centrifuged, resuspended in media, counted and the cells were plated onto a plain plastic material layer.

The keratinocytes were plated at a density of approximately about $10^5$ cells/cm$^2$ in 35 cm$^2$ dishes. The cells were grown in keratinocyte growth media (KGM-modified MCDB 153 containing antibodies by Clonetics of Boulder, Colo.) according to protocols originally developed by Boyce, S. T. and Ham, R. G., *J. of Tissue Culture Meth.* 9:83-93 (1985). The cells were grown for 5-10 days and changed every 2-3 days with keratinocyte growth media with 1.5 mM CaCl$_2$ (hereinafter KGM/1.5 mM CaCl$_2$) until cells reached a 75% confluency by visual observation. All the cultures were incubated in a humidified atmosphere of 5% CO$_2$ at 37° C.

To establish keratinocyte cell cultures as antiproliferative assays, cells prepared as described in the foregoing were washed with PBS and removed from the culture surface with a solution of trypsin/EDTA (0.25%/0.03%). The removed cells were then centrifuged resuspended in the KGM/1.5 mM CaCl$_2$ and counted. The cells were then distributed to 6 well plates at 100,000 cells per well as described in the foregoing. Each well had a volume of 9.5 cm$^2$. After 24-48 hours the cells were changed into KGM/1.5 mM CaCl$_2$. Test compounds were added one to two days later and the cultures maintained for seven days. The media was changed every 2-3 days.

2. Test Solutions

Solutions of the test compounds were prepared as follows: 1 milligram quantities were received in amber glass vials, and stored at $-20°$ C. Sufficient 100% ethanol was added directly to vials to obtain a millimolar solution that was subsequently aliquoted into small amber vials, overlayed with argon gas and stored at $-20°$ C. Each stock solution was thawed once, used and discarded. Aliquots from the stock solutions were diluted directly into medium and then serially diluted from micromolar to $10^{-12}$M concentrations. Dilutions from $10^{-8}$M to $10^{-12}$M had ethanol added for a final concentration of 0.1%. Stock solutions were used within one month. Control cultures were treated with 0.1% ethanol.

3. Cell Proliferation

For each experiment every culture well received the same number of cells from the same culture source. At the termination of the experiment the number of cells per was determined by the following procedure. Wells were washed twice with PBS and then incubated for approximately 10-20 minutes at 37° C. with a trypsin/EDTA solution (0.25%/0.03%). PBS plus 0.1% soybean trypsin was added and the cells were suspended. An aliquot of the cells was placed into isotonic buffered saline and counted on an electronic particle counter (e.g. Coulter Counter ® device by Coulter Electronics of Hialeah, Fla.).

For statistical analysis, the mean was calculated for all wells in each treatment group. Standard error was determined by nonbiased analysis using a value for the number of wells in each group, preferably N=3.

Quantification of proliferation was done by enumerating the number of keratinocyte cells in each well using the Coulter Counter ®. Results shown in Table 1 below show the percent reduction or inhibition of keratinocyte cells calculated for each of 4 concentrations of the compounds tested according to the formula:

$$\left[1 - \left(\frac{\text{mean number of cells in experimental cultures}}{\text{mean number of cells in control cultures}}\right)\right] \times 100$$

TABLE 1

INHIBITION OF COMPOUNDS OF FORMULA I on KERATINOCYTE PROLIFERATION

| Compound | Dosage of Compound (M) | Percent Inhibition on Keratinocyte Proliferation | Standard Deviation N = 3 |
|---|---|---|---|
| 1. ETOH Control | $10^{-6}$ | 0.00 | 24.48 |
| 2. A | $10^{-10}$ | 20.98 | 24.26 |
|  | $10^{-8}$ | 8.24 | 24.26 |
|  | $10^{-7}$ | 10.04 | 26.71 |
|  | $10^{-6}$ | 17.13 | 23.68 |
| 3. B | $10^{-10}$ | 4.52 | 23.77 |
|  | $10^{-8}$ | 22.89 | 24.65 |
|  | $10^{-7}$ | 31.37 | 28.19 |
|  | $10^{-6}$ | 19.46 | 24.46 |

In Table 1, A is [4R-(4α,6β),6[1S-[1α,8β(S), 8aα]]]-6-[2-[1,2,6,7,8,8a -hexahydro-8a-methyl-8-(2-methyl-1-oxo-butoxy)-1-naphthalenyl]-ethyl]tetrahydro-4-hydroxy-2H-pyran-2-one.

In Table 1, B is [1S-(1α,8β,8aβ)]-8-(2-formylethyl)-8a-methyl-1,2,3,4,6,7,8,8a-octahydro-1-naphthalenol-acetate.

Each compound was tested in triplicate. The control (ETOH), as noted above, was 0.1% ethanol.

CONCLUSIONS

The foregoing results evidence that a compound of formula I, compound A, inhibits the proliferation of keratinocyte cells at an inhibition rate of about 20% at a dosage of $10^{-6}$M without toxicity to the cells. Compound B was found to inhibit cell proliferation at a slightly greater rate than compound A of formula I.

The data indicates that a compound of formula I inhibit the proliferation of human keratinocyte cells in vitro, without toxicity to the cells. From these results it can be seen that compounds of formula I are useful as an agent in the treatment of hyperproliferative skin diseases such as psoriasis.

The compounds of formula I are also useful as cholesterol lowering agents. The corresponding hydroxy acids of formula II are also useful as agents for the treatment of hyperproliferative skin diseases and as agents for lowering cholesterol.

DOSAGE FORMS

Oral dosage forms comprising compounds of formula I or II of the invention may be incorporated in capsules, tablets and the like with pharmaceutically acceptable carrier materials.

The useful activity of compounds of formula I as agents for lowering cholesterol is demonstrated by the following test procedures.

INHIBITION OF CHOLESTEROL BIOSYNTHESIS

Materials and Methods

HepG2 cells are maintained in 175 cm$^2$ T flasks in Darlington Medium supplemented with 10% fetal bovine serum (FBS). Darlington Medium consists of 3 parts Minimal Essential Medium, 1 part Waymouth's MAB87/3 medium and $3 \times 10^{-8}$M sodium selenite. This medium is supplemented with 100 U/ml penicillin, 100 ug/ml streptomycin and 2.5 ug/ml Fungizone. In order to establish optimal conditions for the whole cell cholesterol biosynthesis assay, preliminary experiments were performed. 0.25, 0.5, 0.75 or $1 \times 10^6$ cells were seeded into 6 well cluster plates in 2 ml of fully supplemented Darlington Medium. The serum supplemented medium was aspirated after 72 hours and replaced with serum free Darlington Medium with antibiotics. After 24, 48 or 72 hours serum free, the cells received either 0.5 or 1 mCi $^3H_2O$/ml medium. This medium was aspirated after 24 hours and the cells were washed twice with phosphate buffered saline. The cells were frozen overnight at $-20°$ C. after which they were harvested from the wells with 1 ml of trypsin-EDTA. Extracted lipids were separated on an HPLC system; cholesterol peaks were collected and counted in a scintillation counter. Results are expressed as the dpm $^3H_2O$ incorporated into cholesterol.

In the screening assay the cells received compounds at various concentrations concommitantly with $^3H_2O$. When ethanol was the vehicle, the final ethanol concentration was 0.5%, and control wells with that concentration of ethanol were used in each experiment. Results are expressed as the percent dpm $^3H_2O$ incorporated into cholesterol in treated vs control wells. $IC_{50}$ values are calculated using a linear regression analysis.

TABLE 3

Summary of $IC_{50}$ Data (μmolar)
Inhibition of Cholesterol Biosynthesis in HepG2 Cells

| Test | mevinolin | B | A |
|------|-----------|---|-----|
| I    | 0.020     | — | 0.047 |
| II   | 0.64      | — | 3.81 |

As can be seen in the above table, the inhibition of cholesterol biosynthesis of compound A of the invention, as compared to mevinolin, was determined in tests I and II.

CONCLUSIONS

Compound A exhibited cholesterol biosynthesis inhibition as compared to mevinolin, a known active inhibitor of cholesterol biosynthesis. It is noted that there is a large absolute difference between Test I and Test II.

Illustrative of the pharmaceutically acceptable carrier materials which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I or II of the invention include: ointments and creams encompassing formulations having oleaginous, adsorbable, water-soluble and emulsion-type bases such as petroleum, lanolin, polyethylene glycols and the like.

Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like.

Gels are semi-solid preparations made by gelling a solution or suspension of the active ingredient in a carrier vehicle. The vehicles, which can be hydrous or anhydrous, are gelled using a gelling agent, such as carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of inflammation for the exertion of local action. Accordingly, the topical compositions include those pharmaceutical forms in which the compound is applied externally by direct contract with the skin. The topical dosage forms comprise gels, creams, lotions, ointments, powders, aerosols and other conventional forms for applying medications to the skin obtained by admixing the compounds of formula I with known pharmaceutical topical carrier materials. In addition to the application to the skin, the topical compositions of this invention can also be employed in the treatment of inflammations of mucous membranes, where such membranes are accessible to topical application of medication. For example, the topical composition can be applied to the mucous lining of the mouth or lower colon.

The following Examples illustrate the present invention but are not intended to limit its extent in any manner. While the examples describe what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

Unless otherwise stated, percentages and ratios relating to solvent mixtures are expressed in volume, purity data determined by gas chromatography are expressed in area %, and the remaining percentages and ratios are expressed in weight. Temperatures are in degrees celsius (°C.), normal pressure is about 1 atmosphere, and room temperature is about 23° C. Examples were carried out as written unless otherwise indicated.

EXAMPLE 1

(3S,5s)-3-(3-Hydroxypropyl)-5-(1-methylethenyl)-2-methylcyclohexanone

A solution of 63.0 g (0.3 mole) of 3-bromo-n-propyl 1-ethoxyethyl ether was added over 45 minutes to a stirred mixture of 7.2 g (0.3 mole) of Mg turnings in 500 ml of tetrahydrofuran at 5° C. The resulting mixture was stirred at 5° C. for a total of 3 hours to give a brownish suspension. This mixture was then cannulated at 5° C. to a stirred suspension of 3.0 g (15.8 mmole) of copper iodide in 60 ml of tetrahydrofuran at $-28°$ C. After addition, the resulting blue suspension was stirred at $-28°$ C. for 15 minutes, added dropwise with a solution of 22.5 g (150 mmole) of s-carvone in 40 ml of tetrahydrofuran. After addition, it was stirred at $-28°$ C. for 15 minutes, quenched with 200 ml of 2N HCl solution and warmed up to room temperature. After stirring at room-temperature for 1 hr, the mixture was added with 200 ml of water and extracted with 2×600 ml of ether. The combined etheral extracts were washed with 3×120 ml of 3% NH4OH solution, 2×80 ml of brine, dried over MgSO4, filtered and concentrated to give 34 g of the crude (3S,5S)-3-(3-hydroxypropyl)-5-(1-methylethenyl)-2-methylcyclohexanone which was used as such. Analytical sample was obtained by further purification of the crude on a silica gel column (4:1, hexane/EtOAc) IR (CHCl3): 1642,1702,3625 cm$^{-1}$.

$^1$H NMR (200 MHz): δ0.98 (d, J=6.5 Hz, 2H), 1.11 (d, J=6.5 Hz, 1H), 1.34–1.67 (m, 6H), 1.72 (s, 3H), 1.94–2.68 (m, 7H), 3.60 (t, J=6.2 Hz, 2H), 4.69 (d, J=8.3 Hz, 1H). Mass spectrum: M+(210). Anal. for $C_{13}H_{22}O_2$. Calc. for C, 74.24; H, 10.54. Found: C, 74.15; H, 10.90.

EXAMPLE 2

(5S)-5-(3-Hydroxypropyl)-6-methyl-2-cyclohexene-1-one

A solution of 34 g (0.16 mmole) of the crude (3S,5S)-3-(3-hydroxypropyl)-5-(1-methylethenyl)-2-methylcyclohexanone in 600 ml of MeOH at −78° C. was bubbled with ozone until the blue color persisted. Excess ozone was removed by flushing the solution with argon. The reaction mixture was warmed up to −20° C., added with 64.8 g (0.32 mole) of cupric acetate and stirred for 15 minutes. This was then added with 54.2 g (0.195 mole) of ferrous sulfate heptahydrate in small portions. After the addition, the reaction mixture was stirred at −20° C. for 3 hours, room temperature for 1 hr, quenched with 650 ml of water and extracted with 3×1000 ml ether. The aqeous layer was then acidified with 6N HCl until it became homogeneous and extracted with 2×800 ml of ether. The combined etheral extracts were washed with saturated NaHCO3, brine, dried over MgSO4, filtered and concentrated to give 18.5 g of the crude (5S)-5-(3-hydroxypropyl)-6-methyl-2-cyclohexene-1-one which was used as such for the next step. An analytical sample of the conjugated enone was obtained by further purification of the crude (3S,5S)-3-(3-hydroxypropyl)-5-(1-methylethenyl)-2-methylcyclo-hexanone on a silica gel column (2:1, hexane/EtOAc). IR (CHCl3): 1670, 3625 cm$^{-1}$. $^1$H NMR (200 MHz): δ1.04 (d, J=7.3 Hz, 1.5H), 1.17 (d, J=6.9 Hz, 1.5H), 1.43–1.65 (m, 4H), 1.90 (m, 1HO, 2.10–2.27 (m, 2H), 2.34–2.42 (md, 1H), 2.49–2.57 (m, 1H), 3.65 (t, J=6.4 Hz, 2H), 5.98 (mt, 1H), 6.89–6.92 (m, 1H). Mass spectrum m/e: M+ (168). Anal. for $C_{10}H_{16}O_2$: Calc. for C, 71.39; H, 9.59. Found: C, 71.34; H, 9.55.

EXAMPLE 3

(3R)-3-(3-Hydroxypropyl)-2-methylcyclohexanone

A solution of 21.8 g (0.129 mole) of the crude (5S)-5-(3-hydroxypropyl)-6-methyl-2-cyclohexene-1-one in 200 ml of EtOAc was stirred with 1.0 g 10% Pd(C) under 1 atmosphere pressure of hydrogen until a total of 2600 ml of hydrogen was consumed. The reaction mixture was then filtered through a pad of celite which was washed further with EtOAc. The combined filtrates were concentrated to give 22.0 g of the crude ketone which was chromatographed on a silica gel column (4:1, hexane/EtOAc) to give 13.5 g (50% from s-carvone) of the pure (3R)-3-(3-hydroxypropyl)-2-methycyclohexanone. B.P. 110° C./0.15 mmHg. IR (CHCl3): 1702, 3475, 3625 cm$^{-1}$.

$^1$H NMR (200 MHz): δ1.01 (d, J=7.1 Hz, 1H), 1.05 (d, J=6.6 Hz, 2H), 1.33–1.73 (m, 6H) 1.92–2.42 (m, 6H), 2.60 (m, 1H), 3.65 (m, 2H). Mass spectrum: M+ (170). Anal. for $C_{10}H_{18}O_2$: Calc. for C, 70.55; H, 10.66. Found: C, 70.76; H, 10.75.

EXAMPLE 4

(3R)-3-[3-[[(1,1-Dimethylethyl)diphenylsilyl]oxy]-propyl]-2-methyl-cyclohexanone To a solution of 13.5 g (79.6 mmole) of the (3R)-3-(3-hydroxypropyl)-2-methylcyclohexanone in 240 ml of DMF was added 10.82 g (159.2 mmole) of imidazole followed by a dropwise addition of a solution of 26.2 g (95.3 mmole) of t-butylchlorodiphenyl silane in 25 ml of DMF. After addition, the solution was stirred at room temperature for 3 hours, quenched with 260 ml of iced water and extracted with 2×750 ml of ether. The combined etheral extracts were washed with 3×200 ml of water which was back extracted with 2×200 ml of ether. The combined etheral extracts were washed with brine, dried over MgSO4, filtered and concentrated to give 36.4 g of the crude (3R)-3-[3-[[(1,1-dimethylethyl)-diphenylsilyl]oxy]propyl]-2-methylcyclohexanone which was used as such. An analytical sample was obtained by further purification of the above crude on a silica gel column (20:1, hexane/EtOAc). IR (CHCl3): 1130, 1700, 2850 cm$^{-1}$. $^1$H NMR: δ0.98–1.05 (m, 12H), 1.15–1.70 (m, 7HO, 1.89 (m, 2H), 2.05 (m, 1H), 2.15 (m, 1H), 2.25 (m, 1H), 2.40 (m, 1H), 2.55 (m, 1H), 3.65 (m, 2H), 7.38 (m, 6H), 7.66 (m, 4H). Mass spectrum: M+-CH3 (393). Anal. for $C_{26}H_{36}O_2Si$: Calc. for C, 76.42; H, 8.88; Si, 6.87. Found: C, 76.16; H, 9.11; Si, 6.98.

EXAMPLE 5

(R)-2-Methyl-3-[3-[[(1,1-dimethylethyl)diphenylsilyl-]oxy]propyl]-1-cyclohexene-1-butanoic acid ethyl ester A solution of 6.3 g (15.2 mmole) of the (3R)-3-[3-[[(1,1-dimethylethyl)diphenylsilyl]-oxy]propyl]-2-methylcyclohexanone in 150 ml of CH2Cl2 at −12° C. was added with 4.2 ml (20 mmole) of hexamethyldisilazane followed by 2.6 ml (18.2 mmole) of trimethylsilyl iodide. The resulting suspension was stirred at −10° C. for 1 hour, 0° C. for 90 minutes and all the volatiles evaporated. The residual oil was added with 500 ml of pentane and washed with 2×100 ml of chilled NaHCO3 solution. The aqueous layer was then back extracted with 300 ml of pentane and the combined pentane extracts were washed with brine, dried over MgSO4, filtered and concentrated to give 7.58 g (100% crude yield) of the silylenol ether. $^1$H NMR (200 MHz): δ0.15 (s, 9H), 1.05 (s, 9H), 0.90–1.60 (m, 9H), 1.55 (s, 3H), 1.98 (bs, 2H), 3.65 (t, J=6.3 Hz, 2H), 7.40 (m, 6H), 7.70 (m, 4H).

A solution of 7.58 g (15.2 mmole) of the crude silylenol ether in 50 ml of tetrahydrofuran at 0° C. was added with 10.9 ml of a 1.4M solution of MeLi in ether. The mixture was then stirred at 0° C. for 30 minutes, added with a solution of 5.43 g (15.2 mmole) of N-phenyltrifluoromethane sulfonimide in a solution mixture of 30 ml of tetrahydrofuran and 3 ml of hexamethylphosphoramide. After addition, the mixture was warmed up to room temperature, stirred for 45 minutes and stored in the freezer overnight. All the volatiles were removed and the residual oil added with 500 ml of pentane which was washed with 2×200 ml of water. The aqueous layer was then back extracted with 200 ml of pentane. The combined pentane extracts were washed with brine, dried over MgSO4, filtered and concentrated to give 7.54 g (91%) of the crude vinyltrifluoromethane-sulfonate which was used as such. $^1$H NMR (200 Mz): $\delta$1.03 (s, 9H), 1.00–1.95 (m, 9H), 1.74 (s, 3H), 2.12 (s, 1H), 2.28 (s, 1H), 3.65 (t, J=5.5 Hz, 2H), 7.37–7.40 (m, 6H), 7.63–7.67 (m, 4H).

A suspension of 7.26 g (30 mmole) of ethyl-4-iodo-n-butylate and 2.6 g of zinc copper couple in 30 ml of DMF was stirred at 82° C. for 1 hour. The mixture was cooled to room temperature and added with a solution of 7.54 g (13.8 mmole) of the above sulfonate in 10 ml of DMF followed by 173 mg (0.15 mmole) of tetrakis(triphenylphosphine)palladium(0). The resulting mixture was then stirred at 82° C. for 30 minutes, cooled at room temperature and poured into 500 ml of ether. This suspension was then filtered through a bed of celite which was washed with 500 ml of ether. The combined filtrates were then washed with 2×200 ml of 1N HCl and the aqueous layer back extracted with 200 ml of ether. The combined etheral extracts were washed with sat'd NaHCO$_3$, brine, dried over MgSO$_4$, filtered and concentrated. The residual oil was chromatographed on a silica gel column (20:1, hexane/EtOAc) to give 5.56 g (72% from ketone) of the (R)-2-methyl-3-[3-[[(1,1-dimethylethyl)diphenylsilyl]oxy]propyl]-1-cyclohexene-1-butanoic acid ethyl ester as an oil. B.P. 230° C./0.15 mm Hg. $[\alpha]_D^{25}$=−7.3° (CHCl$_3$, c=0.94). IR (CHCl$_3$): 820, 1725 cm$^{-1}$. $^1$H NMR (200 MHz): $\delta$1.05 (s, 9H), 1.25 (t, 6.9 Hz, 3H), 1.24 (m, 2H), 1.45–1.57 (m, 11H), 1.59 (s, 3H), 1.68 (quint. J=7.5 Hz, 2H), 2.27 (t, J=7.3 Hz, 2H), 3.65 (t, J=6.0 Hz, 2H), 4.13 (q, J=7.1 Hz, 2H), 7.35–7.44 (m, 6H), 7.67 (d, J=6.1 Hz, 4H). Mass spectrum: M+-C$_4$H$_8$ (450). Anal. for C$_{32}$H$_{46}$O$_3$Si. Calc. for C, 75.84; H, 9.15; Si, 5.54. Found: C, 75.66; H, 9.18; Si, 5.30.

EXAMPLE 6

[R-(R*,S*)]-(1,1-Dimethylethyl)[3-[3-[4-[(tetrahydro-2H-pyran-2-yl)oxy]butyl]-2-methyl-2-cyclohexene-1-yl]-propoxyl]diphenylsilane To a solution of 15.0 g (29.6 mmole) of (R)-2-methyl-3-[3-[[(1,1-dimethylethyl)diphenylsilyl]oxy]propyl]-1-cyclohexene-1-butanoic acid ethyl ester in 88 ml of tetrahydrofuran at −30° C. was added 1.125 g (29.6 mmole) of lithium aluminum hydride in small portions. The reaction mixture was stirred at −30° C. for 45 minutes, diluted with 300 ml of ether and carefully quenched with 2.25 ml of water followed by 1.8 ml of 10% NaOH. The mixture was stirred at room temperature for an hour, mixed with several teaspoons of MgSO$_4$ and suction filtered through celite which was generously washed with ether. The combined filtrates were concentrated and the crude alcohol was used as such. An analytical sample was obtained by further purification of the crude on a silica gel column (1:1, hexane/EtOAc). IR (CHCl$_3$):820,3620 cm$^{-1}$. $^1$H NMR (200 MHz): $\delta$1.06 (s, 9H), 1.24 (m, 2H), 1.42–1.59 (m, 14H), 1.61 (s, 3H), 1.91 (b, 2H), 200 (hept. J=9.4 Hz, 2H), 3.66 (m, 4H), 7.38 (m, 6H), 7.68 (d, J=7.9 Hz, 2H). Mass spectrum: M+-C$_4$H$_9$ (407). Anal. for C$_{30}$H$_{44}$O$_3$Si: Calc. for C, 77.53; H, 9.54; Si, 6.04. Found: C, 76.82; H, 9.63; Si, 6.04.

To a solution of 13.0 g (27.9 mmole) of above alcohol in 150 ml of CH$_2$Cl$_2$ at room temperature was added 600 mg of pyridinium p-toluenesulfonate followed by 5.8 ml of dihydropyran. The reaction mixture was stirred at room temperature for 2 hours and poured into 100 ml of brine solution. The organic layer was separated and the aqueous layer extracted with 2×200 ml of CH$_2$Cl$_2$. The combined organic extracts were then washed with brine, dried over MgSO$_4$, filtered and concentrated to give 23.8 g of the crude [R-(R*,S*)]-(1,1-dimethylethyl)[3-[3-[4-[(tetrahydro-2H-pyran-2-yl)oxy]butyl]-2-methyl-2-cyclohexene-1-yl]-propoxyl]diphe nylsilane which was used as such for the next step. Analytical sample was obtained by further purification of the crude on a silica gel column (4:1, hexane/EtOAc).

$[\alpha]_D^{25}$=−8.63° (CHCl$_3$,c=1.17). IR (CHCl$_3$): 2990, 822 cm$^{-1}$. $^1$H NMR (200 MHz): $\delta$1.05 (s, 9H), 1.22 (m, 1H), 1.41–1.61 (m, 17H), 1.59 (s, 3H), 1.70 (m, 1H), 1.83–1.89 (b, 1H), 1.98 (hex. J=5.1 Hz, 2H), 3.31–3.52 (m, 2H), 3.66 (t, J=6.0 Hz), 3.70–3.95 (m, 2H), 4.58 (t, J=3.6 Hz, 1H), 7.35–7.42 (m, 6H), 7.67 (d, J=6.2 Hz, 4H). Mass spectrum: M+ (548). Anal. for C$_{35}$H$_{52}$O$_3$Si: C, 76.58; h, 9.55; Si, 5.12. Found: C, 76.30; H, 7.54; Si, 5.32.

EXAMPLE 7

[R-(R*,S*)]-3-[4-[(Tetrahydro-2H-pyran-2-yl)oxy]-butyl]-2-methyl-2-cyclohexene-1-propanol To a solution of 23.8 g (28.0 mmole) of the crude [R-(R*,S*)]-(1,1-dimethylethyl)[3-[3-[4-(tetrahydro-2H-pyran-2-yl)oxy]butyl]-2-methyl-2-cyclohexene-1-yl]-propoxyl]diphenylsilane in 32 ml of tetrahydrofuran was added 45 ml of 1M tetrabutylammonium fluoride in tetrahydrofuran. The reaction mixture was then stirred at room temperature for 3 hours, poured into 100 ml of water and extracted with 3×200 ml of ether. The combined extracts were washed with brine, dried over Na$_2$SO$_4$, filtered and concentrated. The residual oil was chromatographed on a silica gel column (4:1 then 2:1, hexane/EtOAc) to give 8.18 g (94% yield) of [R-(R*,S*)]-3-[4-[(tetrahydro-2H-pyran-2-yl)oxy]butyl]-2-methyl-2-cyclohexene-1-propanol as an oil.

$[\alpha]_D^{25}$=−10.16° (CHCl$_3$, c=1.18). IR (CHCl$_3$): 3620 cm$^{-1}$. $^1$H NMR (200 MHz): $\delta$1.25 (m, 1H), 1.41–1.75 (m, 16H), 1.62 (s, 3H), 1.80–2.09 (m, 7H), 3.38 (m, 1H), 3.50 (m, 1H), 3.64 (bs, 2H), 3.75 (m, 1H), 3.90 (s, 1H), 4.58 (t, J=3.0 Hz, 1H). Mass spectrum: M+ (310). Anal. for C$_{19}$H$_{34}$O$_3$: Calc. for C, 73.50, H, 11.04. Found: C, 73.57; H, 10.70.

EXAMPLE 8

[R-(R*,S*)]-3-[4-[(Tetrahydro-2H-pyran-2yl)oxy]-butyl]-2-methyl-2-cyclohexene-1-propanol acetate To a solution of 8.2 g (25.6 mmole) of [R-(R*,S*)]-3-[4-[(tetrahydro-2H-pyran-2-yl)oxy]butyl]-2-methyl-2-cyclohexene-1-propanol in 30 ml of dry pyridine at 0° C. was added slowly 4.8 ml (51.3 mmole) of acetic anhydride followed by a catalytic amount of 4-dimethylaminopyridine. The solution was stirred at 0° C. for 3 hours and then quenched with iced water. The mixture was extracted with 3×150 ml of CH$_2$Cl$_2$. The organic extracts were acidified with 1N H$_2$SO$_4$, washed with sat'd NaHCO$_3$, dried over MgSO$_4$, filtered and concentrated. The residue was chromatographed on a silica gel column (5:1, hexane/EtOAc), to give 7.3 g (81%) of [R-(R*,S*)]-3-[4-[(tetrahydro-2H-pyran-2-yl)oxy]butyl]-2-methyl-2-cyclohexene-1-propanol acetate as an oil. $[\alpha]_D^{25}$=−11.09° (CHCl$_3$c=1.28). IR (CHCl$_3$): 1730 cm$^{-1}$. $^1$H NMR (200 MHz): $\delta$1.25 (m, 1H), 1.60–1.72 (m, 18H), 1.61 (s, 3H), 1.80–2.05 (m, 4H), 2.05 (s, 3H), 3.38 (m, 1H), 3.50 (m, 1H), 3.72 (m, 1H), 3.88 (m, 1H), 4.05 (m, 2H), 4.58 (t, J=2.6 Hz, 1H). Mass Spectrum: M+ (352). Anal. for C$_{21}$H$_{36}$O$_4$: Calc. for C, 71.55; H, 10.29. Found: C, 71.16; H, 10.41.

EXAMPLE 9

(R)-3[3-(Acetyloxy)propyl]-2-methyl-1-cyclohexene-1-butanol

To a solution of 7.3 g (20.7 mmole) of [R-(R*,S*)]-3-[4-[(tetrahydro-2H-pyran-2yl)oxy]butyl]-2-methyl-2-cyclohexene-1-propanol acetate in 68 ml of absolute ethanol was added 530 mg (2.1 mmole) of pyridinium p-toluenesulfonate and the homogeneous solution heated at 50° C. for 4 hours. The cooled reaction mixture was poured into 280 ml of water and extracted with 3×350 ml of ether. The combined organic extracts were washed with NaHCO$_3$, brine, dried over MgSO$_4$, filtered and concentrated. The crude product was chromatographed on a silica gel column (5:1, hexane/EtOAc) to give 4.3 g (78%) of (R)-3-[3-(acetyloxy)propyl]-2-methyl-1-cyclohexene-1-butanol as an oil. [α]$_D^{25}$ = −15.84° (CHCl$_3$, c=1.01). IR (CHCl$_3$: 1695, 3620 cm$^{-1}$. $^1$H NMR (200 MHz): δ1.21–1.75 (m, 17H), 1.61 (s, 3H), 1.91–2.05 (m, 4H), 3.65 (t, J=6.6 Hz, 2H), 4.05 (m, 2H). Mass spectrum: M+ (268). Anal. for C$_{16}$H$_{28}$O$_3$: Calc. for C, 71.60; H, 10.52. Found: C, 71.74; H, 10.46.

EXAMPLE 10

(R)-3-[3-(acetyloxy)propyl]-2-methyl-1-cyclohexene-1-butanol

To a solution of 2.9 ml (30.6 mmole) of oxalyl chloride in 80 ml of CH$_2$Cl$_2$ at −50° C. was added a solution of 4.74 ml (61.2 mmole) of DMSO in 14.0 ml of CH$_2$Cl$_2$. This mixture was then stirred at −50° C. for another 5 minutes and added slowly with 4.1 g (15.3 mmole) of (R)-3-[3-(acetyloxy)propyl]-2-methyl-1-cyclohexene-1-butanol in 16.3 ml of CH$_2$Cl$_2$. The mixture was then stirred at −50° C. for another 35 minutes and added with 20.0 ml (143 mmole) of triethylamine to give a white suspension. After stirring at −50° C. for 5 minutes, the mixture was stirred at room temperature for 10 minutes, added with 20 ml of water and extracted with 2×300 ml of CH$_2$Cl$_2$. The combined extracts were then washed with 2×50 ml of water, brine, dried over Na$_2$SO$_4$, filtered and concentrated. The crude product was chromatographed on a silica gel column (6:1, hexane/EtOAc) to give 3.6 g (87.8%) of the unstable (R)-3-[3-(acetyloxy)propyl]-2-methyl-1-cyclohexene-1-butanal as an oil. [α]$_D^{25}$ = −17.11° (CHCl$_3$, c=1.04). IR (CHCl$_3$): 1725, 2725 cm$^{-1}$. $^1$H NMR (200 MHz): δ1.25 (m, 1H), 1.61 (s, 3H), 1.56–1.75 (m, 10H), 1.91 (n, 2H), 2.05 (s, 3H), 1.95–2.10 (m, 2H), 2.40 (dt, J=1.8, 7.3 Hz, 2H), 4.06 (m, 2H), 9.77 (t, J=1.8 Hz, 1H). Mass spectrum: M+ (266). Anal. for C$_{16}$H$_{26}$O$_3$: Calc. for C, 72.14; H, 9.80. Found: C, 70.12; H, 9.72.

EXAMPLE 11

[1S-(1α,8β,8aβ)]-8-[(3-Acetyloxy)propyl]-1,2,3,4,6,7,8,8a-octahydro-8a-methyl-1-naphthalenol To a stirred solution of 4.65 g (17.5 mmole) of (R)-3-[3-(acetyloxy)propyl]-2-methyl-1-cyclohexene-1-butanol in 175 ml of CH$_2$Cl$_2$ at −78° C. was added 53 ml (53 mmole) of 1M dimethylaluminum chloride in hexane. After addition, the reaction flask was transferred to a −30° C. bath. The reaction mixture was then stirred at −30° C. for 60 minutes, −10° C. for 60 minutes and cannulated to a 200 ml of ice-water mixture. The combined mixture was then extracted with 3×300 ml of ether. The combined organic extracts were then washed with brine, dried over MgSO$_4$, filtered and concentrated. The residual oil was eluted on a silica gel column (2:1, hexane/EtOAc) to give 2.94 g (63%, 67% pure) of [1S-(1α,8β,8aβ)]-8-[(3-Acetyloxy)propyl]-1,2,3,4,6,7,8,8a-octahydro-8a-methyl-1-naphthalenol. $^1$H NMR (200 MHz): δ0.93 (s, 3H), 1.10–2.40 (m, 16H), 2.04 (s, 3H), 3.75 (s, 1H), 4.10 (m, 2H), 5.55 (s, 1H). $^{13}$C NMR (25.2 MHz): δ17.87 (angular methyl), 20.45, 20.96, 23.04, 24.67, 25.84, 27.06, 28.88, 31.45, 37.37, 43.18, 64.76, 71.19, 139.74, 171.18.

EXAMPLE 12

[1R-(1α,8β,8aα)]-8-(Acetyloxy)-8a-methyl-1,2,3,4,6,7,8,8a-octahydro-1-naphthalenepropanol A solution of 5.2 g of [1S-(1α,8β,8aβ)]-8-[(1-acetyloxy)propyl]-1,2,3,4,6,7,8,8a-octahydro-8a-methyl-8-naphthalenol in 30 ml of pyridine at 0° C. was added with 6 ml of acetic anhydride followed by catalytic amount of 4-dimethylaminopyridine. The solution was stirred at 0° C. for 3 hours, warmed up to room temperature and stirred for 4 hours. The mixture was quenched with water, acidified with 6N HCl and extracted with ether. The ethereal extracts were then washed with NaHCO$_3$, brine, dried over MgSO$_4$, filtered and concentrated to give 5.6 g of the crude acetate. $^1$H NMR (200 MHz: δ0.98 (s, 3H), 1.70 (s, 3H/3, vinylmethyl group), 2.04 (s, 3H), 2.05 (s, 3H), 1.20–2.40 (m, 14H), 2.70 (m, 2H), 5.00 (s, 1H/3), 5.05 (s, 2H/3), 5.50 (s, 1H).

The above crude acetate was dissolved in 60 ml of tetrahydrofuran and added with 20 ml each of MeOH and water. This solution was then cooled at 0° C., added with 903 mg of LiOH.H$_2$O. This mixture was then stirred at 0° C. for 3 hours, room temperature for 2 hours, poured into 200 ml of water and extracted with 3×200 ml of EtOAc. The combined extracts were washed with diluted HCl solution, NaHCO$_3$, brine, dried over MgSO$_4$, filtered and concentrated. Small scale separation of the mixture gave 70–80% yield of [1R-(1α,8β,8aα)]-δ-(acetyloxy)-8a-methyl-1,2,3,4,6,7,8,8a-octahydro-1-naphthalenepropanol based on the theoretical amount of the desired ene product. Repetitive purification of the crude on a HPLC column (1:4-1:2, hexane/EtOAc) provided the pure [1R-(1α,8β,8aα)]-8-(acetyloxy)-8a-methyl-1,2,3,5,7,8,8a-octahydro-1-naphthalenepropanol.

[α]$_D^{25}$ = −43.08° C. (CHCl$_3$, c=0.26). IR (CHCl$_3$): 1662, 1723, 3570 cm$^{-1}$. $^1$H NMR (200 MHz): δ0.96 (s, 3H), 1.23–1.79 (m, 12H), 2.04 (s, 3H), 1.91–2.01 (m, 3H), 2.25 (m, 1H), 3.56 (m, 2H), 5.08 (s, 1H), 5.44 (s, 1H). $^{13}$C NMR (25.2 MHz): δ18.12 (angular methyl group), 21.23, 21.35, 23.13, 24.52, 25.81, 26.74, 31.28, 31.66, 37.98, 41.60, 62.82, 74.11, 122.90, 139.68, 171.00. Mass spectrum: M+ (266). Anal. for C$_{16}$H$_{26}$O$_3$: Calc. for C, 72.14; H, 9.84. Found: C, 72.00; H, 9.90.

EXAMPLE 13

[1S-(1α,8β,8aβ)]-8-(2-Formylethyl)-8a-methyl-1,2,3,4,6,7,8,8a-octahydro-1-naphthalenol acetate To a stirred suspension of 1.27 g (4.77 mmole) of [1R-(1α,8β,8aα)]-8-(acetyloxy)-8a-methyl-1,2,3,4,6,7,8,8a-octahydro-1-naphthalenepropanol, 3.2 g florasil and 117 mg of NaOAc in 48 ml of CH$_2$Cl$_2$ at room temperature was added 1.55 g (7.16 mmole) of pyridinium chlorochromate. The resulting suspension was stirred at room temperature for 5 hours, poured into 500 ml of ether and stirred for 30 minutes. The mixture was then filtered through a bed of florasil which was further washed with 3×300 ml of ether. The combined filtrates were concentrated and the residue purified on a silica gel column (1:4, EtOAc/hexane) to give 957 mg (75%) of [1S-(1α,8β,8aβ)]-8-(2-formylethyl)-8a-methyl-1,2,3,4,6,7,8,8a-octahydro-1-naphthalenol acetate.

M.P.=71.0°-71.5° C. (hexane). $[\alpha]_D^{25}=-21.18°$, (CHCl$_3$, c=0.53). Ir (CHCl$_3$): 2725, 1722 cm$^{-1}$. $^1$H NMR (200 MHz): δ1.00 (s, 3H), 1.18-1.40 (m, 2H), 1.51-1.62 (m, 4H), 1.75-1.85 (m, 3H), 2.05 (s, 3H), 1.89-2.09 (m, 3H), 2.33 (m, 3H), 5.05 (s, 1H), 5.46 (s, 1H), 9.69 (s, 1H). $^{13}$C NMR (25.2 MHz): δ17.94, 21.01, 21.08, 21.27, 22.70, 25.52, 26.42, 31.51, 37.54, 41.47, 42.27, 73.78, 122.74, 139.36, 170.58. Mass spectrum: M$^+$ (264). Anal. for C$_{16}$H$_{24}$O$_3$: Calc. for C, 72.69; H, 9.15. Found: C, 72.79; H, 8.83.

EXAMPLE 14

[1R-[1β(R*),8α,8aβ]]-6-[2-[8(Acetyloxy)-1,2,3,5,6,7,8,8a-octahydro-8a-methyl-1-naphthalenyl]-ethyl]-5,6-dihydro-4H-pyran-4-one A solution of 531 mg (2.01 mmole) of [1S-(1α,8β,-8aβ)]-8-(2-formylethyl)-8a-methyl-1,2,3,4,6,7,8,8a-octahydro-1-naphthalenol acetate in 20 ml of CH$_2$Cl$_2$ at −78° C. was added with 2.4 ml of 1M TiCl$_4$ in CH$_2$Cl$_2$, stirred for 2 minutes, transferred to a −40° C. bath, stirred for another minute and added with 0.77 ml (4.8 mmole) of 1-methoxy-3-trimethylsiloxyl-butadiene in 5 ml of CH$_2$Cl$_2$. The dark red reaction mixture was allowed to stir at −40° C. for 60 minutes, added with another 0.77 ml of the diene in 5 ml of CH$_2$Cl$_2$ and stirred for another 20 minutes. The reaction mixture was then quenched with 10 ml of sat'd NaHCO$_3$ solution, stirred at room temperature for 10 minutes and poured into a mixture of NaHCO$_3$ (50 ml), NaCl (200 ml) and EtOAc (600 ml). After vigorous shaking, the organic layer was separated, dried over Na$_2$SO$_4$, filtered through a bed of MgSO$_4$ and concentrated. The red residue was then added to a premixed solution of tetrahydrofuran (80 ml) and CF$_3$COOH (10 ml) and stirred at room temperature for 1.5 hour. The mixture was then added with 3 g of solid NaHCO$_3$ and sat'd NaHCO$_3$ until bubbling stopped. The mixture was then poured into 200 ml of brine and extracted with 600 ml of EtOAc. The organic layer was separated, dried over MgSO$_4$, filtered and concentrated. The residue was added with 300 ml of CHCl$_3$, decolorized with activated charcoal, filtered through a bed of celite and filtrate concentrated. The residue was purified on a silica gel column (2.5:1, hexane/EtOAc) to give 291 mg (44%) of [1R-[1β(R*),8α,8a β]]-6-[2-8-(acetyloxy)-1,2,3,5,6,7,8,8a-octahydro-8a-methyl-1-naphthalenyl]-ethyl]-5,6-dihydro-4H-pyran-4-one as an oil. Ir (CHCl$_3$): 1670, 1722 cm$^{-1}$. $^1$H NMR (200 MHz): δ0.98 (s, 3H), 1.09-2.08 (m, 14H), 2.01 (s, 3H), 2.42-2.49 (m, 3H), 4.32 (m, 1H), 5.03 (s, 1H), 5.36 (d, J=5.7 Hz, 1H), 5.45 (s, 1H), 7.32 (d, J=5.8 Hz, 1H). $^{13}$C NMR (25.2 MHz): δ18.04, 21.05, 21.28, 22.98, 23.65, 25.63, 26.43, 31.50, 32.94, 37.77, 41.42, 42.07, 73.86, 79.18, 106.88, 122.76, 139.48, 163.22, 170.28, 192.66; HRMS (C$_{20}$H$_{28}$O$_4$): Calc. for M$^+$ 332.1988. Obs. 332.1966. Anal. for C$_{20}$H$_{28}$O$_4$: Calc. for C, 72.26; H, 8.49. Found: C, 71.58; H, 8.36.

EXAMPLE 15

[1R-[1β(1R*,6S*),8α,8aβ]]-2-[2-[8-(Acetyloxy)-1,2,3,5,6,7,8,8a-octahydro-8a-methyl-1-naphthalenyl]ethyl]tetrahydro-6-methoxy-4H-pyran-4-one A solution of 291 mg (0.88 mmole) of [1R-[1β(R*),8α,8aβ]]-6-[2-[8-(acetyloxy)-1,2,3,5,6,7,8,8a-octahydro-8a-methyl-1-naphthalenyl]-ethyl]-5,6-dihydro-4H-pyran-4-one in 25 ml of MeOH at room temperature was added with 2 ml of triethylamine and stirred at room temperature for 24 hours. All volatiles were evaporated and residue purified on a silica gel column (2:1, hexane/EtOAc) to give 163 mg (51%) of [1R-[1β(1R*,6S*),8α,8aβ]]-2-[2-[8-(acetyloxy)-1,2,3,5,6,7,8,8a-octahydro-8a-methyl-1-naphthalenyl]-ethyl]tetrahydro-6-methoxy-4H-pyran-4-one along with the starting enones and equatorial isomer (99% recovery). $[\alpha]_D^{25}=+34.29°$ (CHCl$_3$, c=0.21). Ir (CHCl$_3$): 1722 cm$^{-1}$. $^1$H NMR (200 MHz): δ0.95 (s, 3H), 1.14-1.80 (m, 12H), 2.01 (s, 3H), 1.92-2.15 (m, 2H), 2.21-2.45 (m, 4H), 2.60 (dd, J=4.6, 15.2 Hz, 1H), 3.30 (s, 3H), 3.90 (m, 1H), 5.06 (bs, 2H), 5.43 (s, 1H). $^{13}$C NMR (25.2 MHz): δ18.04, 21.09, 21.18, 23.14, 24.48, 25.71, 26.58, 31.55, 35.12, 38.81, 41.45, 46.60, 47.45, 54.65, 68.92, 73.75, 99.33, 122.76, 139.54, 170.27. HRMS (EI): Calc. M$^+$ (C$_{21}$H$_{32}$O$_5$), 364.2250. Obs. 364.2275.

EXAMPLE 16

[2S-(2α,4α,6β),6[1S-[1α,8α(S),8aα]]]-6-[2-[8-(Acetyloxy)-1,2,3,5,6,7,8,8a-octahydro-8a-methyl-1-naphthalenyl]ethyl]tetrahydro-2-methoxy-2H-pyran-4-ol A solution of 163 mg (0.45 mmole) of [1 R-[1β(1R*,6S*),8α,8aβ]]-2-[2-[8-(acetyloxy)-1,2,3,5,6,7,8,8a-octahydro-8a-methyl-1α-methyl-1-naphthalenyl]-ethyl]tetrahydro-6methoxy-H-pyran-4-one in 9 ml of tetrahydrofuran at −78° C. was added with 0.58 ml (0.58 mmole) of 1M L-selectride ® in tetrahydrofuran. The resulting solution was allowed to stir at −78° C. for 1.5 hour, quenched with 0.9 ml of 2N NaOH solution, warmed up to room temperature, added with 0.27 ml of 30% H$_2$O$_2$ and stirred at room temperature for another 30 minutes. The mixture was then poured into 50 ml of water which was extracted with 2×70 ml of EtOAc. The combined EtOAc extracts were washed with brine, dried over MgSO$_4$, filtered and concentrated. Purification of the residue on a silica gel column (2:1, hexane/EtOAc) gave 145 mg (89%) of [2S-(2α,-4α,6β), 6[1S-[1α,8β(S),8a α]]]-6-[2-[8-(acetyloxy)-1,2,3,5,6,7,8,8a-octahydro-8a-methyl-1-naphthalenyl]ethyl]tetrahydro-2-methoxy-2H-pyran-4-ol as a colorless oil. $[\alpha]_D^{25}=+41.78°$ C. (CHCl$_3$, c=0.45). Ir (CHCl$_3$): 1723, 3523 cm$^{-1}$. $^1$H NMR (200 MHz): δ0.95 (s, 3H), 0.99-2.05 (m, 18H), 2.01 (s, 3H), 2.23 (m, 1H), 3.33 (s, 3H), 3.56 (d, J=10.1 Hz, 1H), 3.84-4.02 (m, 2H), 4.79 (s, 1H), 5.03 (s, 1H), 5.43 (s, 1H). Anal. for C$_{21}$H$_{34}$O$_5$: Calc. for C, 68.82; H, 9.35. Found: C, 68.48; H, 9.45.

EXAMPLE 17

[1aS-[1aα,4β,4(2R,4R,6S),4aβ,5α,8aα]]-Deca hydro-4-[2-[tetrahydro-6-methoxy-4-[[(1,1-dimethylethyl)dimethylsilyl]oxy]-2H-pyran-2-yl]ethyl]-4a-methyl-3H-naphth[1,8a-b]oxiren-5-ol A solution of 145 mg (0.4 mmole) of [2S-(2α,4α,6β), 6[1S-[1α,8β(S),8aα]]]-6-[2-[8-(acetyloxy)-1,2,3,5,6,7,8,8a-octahydro-8a-methyl-1-naphthalenyl]-ethyl]tetrahydro-2-methoxy-2H-pyran-4-ol in 3 ml of DMF was added with 50 mg (0.8 mmole) of imidazole and 90 mg (0.6 mmole) of t-butyldimethylsilyl chloride. The solution was stirred at 60° C. for 3 hours, room temperature for 12 hours, poured into 50 ml of water and extracted with 2×100 ml of ether. The combined etheral extracts were washed with brine, dried over MgSO4, filtered and concentrated. The residue was chromatographed on a silica gel column (10:1, hexane/EtOAc) to give 177 mg (92%) of the silyl ether. $[\alpha]_D^{25} = +32.76°$ (CH2Cl2, c=0.29). Ir (CHCl3): 835, 1722 cm$^{-1}$. $^1$H NMR (200 MHz): δ0.035 (s, 3H), 0.044 (s, 3H), 0.89 (s, 9H), 0.98 (s, 3H), 1.07 (m, 2H), 1.23–1.42 (m, 2H), 1.48–1.71 (m, 8H), 1.78–1.84 (m, 3H), 1.99 (m, 2H), 2.05 (s, 3H), 2.08 (m, 1H), 2.30 (m, 1H), 3.31 (s, 3H), 4.03–4.05 (m, 2H), 4.68 (t, J=3.2 Hz, 1H), 5.06 (t, J=2.8 Hz, 1H), 5.47 (s, 1H). Mass spectrum: M$^+$-MeOH-HOAc (388). Anal. for C27H48O5Si: Calc. for C, 67.45; H, 10.06; Si, 5.84. Found: C, 67.11; H, 10.10; Si, 5.94.

A solution of 177 mg (0.37 mmole) of the above acetate in 4.4 ml of a solvent mixture of ether and tetrahydrofuran (10 to 1) at −78° C. was added with 1.1 ml of 1M Dibal-H in hexane. The resulting solution was allowed to stir ar −78° C. for 90 minutes, quenched with 2 ml of water, warmed up to room temperature, poured into 50 ml of water and extracted with 2×100 ml of EtOAc. The combined EtOAc extracts were washed with 20 ml of 0.1N NaOH, brine, dried over MgSO4, filtered and concentrated. The residue was chromatographed on a silica gel column (4:1, hexane/EtOAc) to give 113 mg (70%) of the [1S-[1α,8β,8(2R,2α,4β,6β),8aβ]]-1,2,3,4,6,7,8,8a-octahydro-8-[2-[tetrahydro-6-methoxy-4-[[(1,1-dimethylethyl)dimethylsilyl]oxy]-2H-pyran-2-yl]ethyl]-8a-methyl-1-naphthalenol as a clear oil. Ir (CHCl3): 838, 3620 cm$^{-1}$. $^1$H NMR (200 MHz): δ0.11 (s, 3H), 0.26 (s, 3H), 0.87 (s, 9H), 0.92 (s, 3H), 1.00–1.40 (m, 3H), 1.55–2.03 (m, 14H), 2.25 (m, 1H), 3.31 (s, 3H), 3.81 (bs, 1H), 4.00–4.14 (m, 2H), 4.68 (t, J=3.9 Hz, 1H), 5.54 (s, 1H). Mass spectrum: M$^+$-MeOH (406).

To a stirred suspension of 113 mg (0.26 mmole) of the above alcohol and 210 mg of Na2CO3 in 10 ml of CH2Cl2 at 0° C. was added 111 mg (0.52 mmole) of 3-chloroperbenzoic acid. The mixture was stirred at 0° C. for 1 hour, quenched with 1 ml of dimethylsulfide, warmed up to room temperature and stirred for 10 minutes. After pouring into 50 ml of CH2Cl2, the mixture was filtered and concentrated. The residue was chromatographed on a silica gel column (4:1, hexane/EtOAc) to give 102 mg (86.4%) of [1aS-[1aα,4β,4(2R,4R,6S),4aβ,5α,8aα]]-decahydro-4-[2-[tetrahydro-6-methoxy-4[[(1,1-dimethylethyl)dimethylsilyl]oxy]-2H-pyran-2-yl]ethyl]-4a-methyl-3H-naphth[1,8a-b]oxiren-5-ol as an oil.

$[\alpha]_D^{25} = +38.39°$ (in CHCl3, c=0.29). Ir (CHCl3): 3656 cm$^{-1}$. $^1$H NMR (200 MHz): δ0.00 (s, 3H), 0.012 (s, 3H), 0.85 (s, 9H), 0.95 (s, 3H), 1.05–2.80 (m, 19H), 2.62 (d, OH, J=9.4 Hz, 1H), 2.80 (bs, 1H), 3.28 (s, 3H), 3.86 (d, J=9.4 Hz, 1H), 4.00 (m, 2H), 4.65 (t, J=3.6 Hz, 1H). $^{13}$C NMR (25.2 MHz): δ−7.93, 15.33, 17.14, 18.08, 21.09, 22.84, 24.68, 25.84, 29.10, 31.14, 33.16, 34.31, 37.07, 39.27, 39.87, 54.87, 58.15, 63.97, 64.94, 65.43, 71.89, 98.13. Mass spectrum: M$^+$-H2O (436). Anal. for C25H46O5Si: Calc. for C, 66.03; H, 10.20; Si, 6.18. Found: C, 65.96; H, 10.51; Si, 6.32.

EXAMPLE 18

[1S-[1α,8β,8(2R,2α,4β,6β),8aβ]]-1,2,3,6,7,8,-Hexahydro-8-[2-[tetrahydro-6-methoxy-4-[[(1,1-dimethylethyl)-dimethylsily]oxy]-2H-pyran-2-yl]ethyl]-8a-methyl-1-naphthalenol To a solution of 200 mg (0.64 mmole) of diphenyldiselenide in 3 ml of EtOH was added 73 mg (1.92 mmole) of sodium borohydride in small portions. The resulting solution was then added with 89 mg (0.16 mmole) of [1aS-[1aα,4β,4(2R,4R,6S),4aβ,5α,8a α]]-decahydro-4-[2-tetrahydro-6-methoxy-4-[[(1,1-dimethylethyl)-dimethylsilyl]oxy]-2H-pyran-2-yl]ethyl]-4a-methyl-3H-naphth[1,8a-b]oxiren-5-ol in 1.5 ml of EtOH and heated at 90° C. overnight. The cooled reaction mixture was then eluted on a silica gel column (5:1, hexane/EtOAc) to give the diol contaminated with diphenyldiselenide. $^1$H NMR (200 MHz): δ0.022 (s, 3H), 0.035 (s, 3H), 0.88 (s, 9H), 0.96 (s, 3H), 1.10–1.90 (m, 17H), 2.00–2.60 (m, 3H), 3.12 (d, J=3.3 Hz, 1H), 3.34 (s, 3H), 3.91 (m, 1H), 4.04 (m, 1H), 4.25 (m, 1H), 4.70 (t, J=3.6 hz, 1H), 4.94 (s, 1H), 7.21 (m, 3H), 7.52 (m, 2H). Ir (CHCl3): 688, 832, 3410 cm$^{-1}$. Mass spectrum: M$^+$ (612).

The above mixture was then dissolved in 3 ml of tetrahydrofuran, added with 0.5 ml of pyridine, 0.2 ml of 30% H2O2 and heated at 50° C. for 10 minutes. The cooled reaction mixture was then quenched with 1 ml of saturated Na2S2O3, stirred for 20 minutes, poured into EtOAc, washed with brine, dried over MgSO4, filtered and concentrated. Purification of the residue on a silica gel column (3:1, hexane/EtOAc) to afford 60 mg (68% from epoxide) of the allylic alcohol. $^1$H NMR (200 MHz): δ0.006 (s, 3H), 0.022 (s, 3H), 0.74 (s, 3H), 0.87 (s, 9H), 1.18–2.10 (m, 15H), 2.32 (m, 1H), 2.41 (d, J=6.9 Hz, 2H), 3.31 (s, 3H), 3.77 (d J=8.7 Hz, 1H), 4.00–4.19 (m, 3H), 4.68 (t, J=3.51 Hz, 1H), 5.50 (d, J=9.6 Hz, 1H), 5.77 (dd, J=3.6, 9.6 Hz, 1H).

A solution of 60 mg (0.11 mmole) of the above diol in 4 ml of CH2Cl2 was added with 28 mg (0.11 mmole) of pyridinium p-toluenesulfonate and stirred at room temperature for 2 hours. The reaction mixture was poured into a 40 ml solution mixture of brine (30 ml) and saturated NaHCO3 (10 ml) and extracted with 2×70 ml of CH2Cl2. The CH2Cl2 extracts were then dried over MgSO4, filtered and concentrated. Purification of the crude on a silica gel column (6:1, hexane/EtOAc) gave 39 mg (65%) of [1S-[1α,8β,8-(2R,2α,4β,6β),8aβ]]-1,2,3,6,7,8-hexahydro-8-[2-[tetrahydro-6-methoxy-4-[[(1,1-dimethylethyl)dimethylsily]oxy]-2H-pyran-2-yl]ethyl]-8a-methyl-1-naphthalenol.

$[\alpha]_D^{25} = +33.33°$ (CHCl3, c=0.03). Ir (CHCl3): 838, 3460, 3605 cm$^{-1}$. $^1$H NMR (200 MHz): δ0.013 (s, 3H), 0.029 (s, 3H), 0.88 (bs, 12H), 1.21–1.40 (m, 3H), 1.53–1.98 (m, 9H), 2.14–2.35 (m, 4H), 3.32 (s, 3H), 3.91 (bs, 1H), 4.05 (m, 2H), 4.68 (t, J=4.2 Hz, 1H), 5.45 (bs, 1H), 5.59 (dd, J=5.2, 9.6 Hz, 1H), 5.96 (d, J=9.6 Hz, 1H). HRMS: Calc. for C26H44O4Si: M$^+$-H2O-MeOH: 386.2641. Obs.: 386.2638.

EXAMPLE 19

[4R-(4α,6β), 6[1S-[1α,8β(S),8aα]]]-6-[2-[1,2,6,7,8,8a-Hexahydro-8a-methyl-8-(2-methyl-1-oxo-butoxy)-1-naphthalenyl]ethyl]tetrahydro-4-hydroxy-2H-pyran-2-one To a solution of 40 mg (0.092 mmole) of [1S-[1α,8β,8-(2R,2α,4β,6β), 8aβ]]-1,2,3,6,7,8-hexahydro-8-[2-[tetrahydro-6-methoxy-4-[[(1,1-dimethylethyl)dimethylsilyl]oxy]-2H-pyran-2-yl]ethyl]-8a-methyl-1-naphthalenol in 4 ml of $CH_2Cl_2$ was added 112 mg (0.92 mmole) of 4-dimethylaminopyridine, 0.104 ml (0.92 mmole) of (S)-(+)-2-methylbutyric acid and 190 mg (0.92 mmole) of 1,3-dicyclohexylcarbodiimide. The reaction mixture was then stirred at room temperature overnight, poured into 100 ml of $CH_2Cl_2$, filtered and concentrated. The residue was purified on a silica gel column (15:1, hexane/EtOAc) to give 40 mg (82%) of the ester. $[\alpha]_D^{25} = +177.78°$ ($CHCl_3$, c=0.045). Ir ($CHCl_3$): 835, 1720 $cm^{-1}$. $^1$H NMR (200 MHz): δ0.024 (s, 3H), 0.87 (m, 12H), 0.94 (s, 3H), 1.11 (d, J=6.8 Hz, 1H), 1.25–1.95 (m, 16H), 2.11 (bs, 1H), 2.39 (m, 2H), 3.29 (s, 3H), 4.02 (m, 2H), 4.67 (t, J=3.7 Hz, 1H), 5.03 (s, 1H), 5.46 (s, 1H), 5.63 (m, 1H), 5.92 (d, J=9.5 Hz, 1H). HRMS (FAB): Calc. for M++H, 521.3662 ($C_{30}H_{53}O_5Si$). Obs. 521.3644.

To a solution of 20 mg (0.038 mmole) of the above ester in 4 ml of tetrahydrofuran was added 2 ml of 10% HCl. The mixture was stirred at room temperature for 2 hours, poured into a 30 ml mixture of $NaHCO_3$ (10 ml) and brine (20 ml) and extracted with 2×75 ml of EtOAc. The organic layer was dried over $MgSO_4$, filtered and concentrated to give the 19 mg of the crude lactol. The above crude lactol was dissolved in 12 ml of benzene and added with 1.2 g of freshly prepared $AgCO_3$/celite. The mixture was heated at 100° C. to distill off 6 ml of benzene and heated again at 95° C. for 2 hours. The cooled mixture was poured into 100 ml of EtOAc and filtered through a bed of celite. The filtered cake was again washed with 2×50 ml of EtOAc and the combined filtrates were concentrated. The crude product was chromatographed on a silica gel column (1:3, hexane/EtOAc) to give 8.7 mg (58%) of [4R-(4α,6β), 6[1S-[1α/8β(S), 8a,α]]]-6-[2-[1,2,6,7,8,8a-hexahydro-9a-methyl-8-2-methyl-1-oxo-butoxy)-1-naphthalenyl]ethyl]tetrahydro-4-hydroxy-2H-pyran-2-one. M.P. 89.5°–90.0° C. hexane/ether. $[\alpha]_D^{25} = +115.63°$ ($CH_2Cl_2$, c=0.16) Ir ($CHCl_3$): 1718, 3610 $cm^{-1}$. $^1$H NMR (200 MHz): δ0.88 (t, J=7.5 Hz, 3H), 0.95 (s, 3H), 1.11 (d, J=6.7 Hz, 3H), 1.20–2.45 (m, 17H), 2.61 (dd, J=2.7, 18.3 Hz, 1H), 2.73 (dd, J=4.7, 17.5 Hz, 1H), 4.34 (bs, 1H), 4.58 (m, 1H), 5.08 (s, 1H), 5.45 (s, 1H), 5.59 (dd, J=5.5, 9.0 hz, 1H), 6.00 (d, J=5.1 Hz, 1H). Mass spectrum: M+ (390). Anal. for $C_{23}H_{34}O_5$: Calc. C, 70.72; H, 8.78. Found: C, 70.36; H, 8.80.

EXAMPLE 20

[4R-[4β,6β,6[8S(8α,8aβ)]]]-6-[2-[1,2,6,7,8,8a-Hexahydro-8-(2,2-dimethyl-1-oxobutoxy)-8a-methyl-1-naphthalenyl]ethyl]tetrahydro-4-hydroxy-2H-pyran-2-one A solution of 35 mg (0.064 mmole) of [1S-[1α,8β,8(2R,2α,4β,6β), 8aβ]]-1,2,3,6,7,8-hexahydro-8-[2-[tetrahydro-6-methoxy-4-[[(1,1-dimethylethyl)dimethylsilyloxy]-2H-pyran-2-yl]ethyl]-8a-methyl-1-naphthalenol in 0.5 ml of pyridine was added with few crystals of 4-dimethylaminopyridine and 0.05 ml of 2,2-dimethylbutyryl chloride. The mixture was heated at 65° C. overnight, an additional 0.15 ml of acid chloride was added, and the mixture heated at 95° C. for 4 hours. The cooled mixture was diluted with 150 ml of ether, washed with diluted HCl solution, sat'd $NaHCO_3$, brine, dried over $MgSO_4$, filtered and concentrated. The residue was purified on a silica gel column to give 30 mg (71.4%) of the ester. $^1$H NMR (200 MHz): δ0.003 (s, 3H), 0.027 (s, 3H), 0.82 (t, J=7.4 Hz, 3H), 0.87 (s, 9H), 0.94 (s, 3H), 1.11 (s, 6H), 1.20–2.30 (m, 17H), 3.29 (s, 3H), 4.01 (m, 2H), 4.68 (t, J=2.4 Hz, 1H), 5.00 (bs, 1H), 5.44 (bs, 1H), 5.60 (m, 1H), 5.97 (d, J=10.1 Hz, 1H).

To a solution of 30 mg (0.046 mmole) of the above ester in 4 ml of tetrahydrofuran was added 2 ml of 10% HCl. The mixture was stirred at room temperature for 3.5 hours, poured into a 50 ml of $NaHCO_3$ water and extracted within 2×50 ml of EtOAc. The organic layer was washed with brine, dried over $MgSO_4$, filtered and concentrated to give crude lactol. The above crude lactol was dissolved in 18 ml of benzene and 1.7 g of freshly prepared $AgCO_3$/celite was added. The mixture was heated at 100° C. to distill off 9 ml of benzene and heated again at 95° C. for 2.5 hours. The cooled mixture was poured into 100 ml of EtOAc and filtered through a bed of celite. The filtered cake was again washed with 2×50 ml of EtOAc and the combined filtrates were concentrated. The crude product was chromatographed on a silica gel column (1:3, hexane/EtOAc) to give 12.5 mg (68%) of [4R-[4β,6β,6[8S(8α,8aβ)]]]-6-[2-[1,2,6,7,8,8a-hexahydro-8-(2,2-dimethyl-1-oxobutoxy)-8a-methyl-1-naphthalenyl]ethyl]tetrahydro-4-hydroxy-2H-pyran-2-one. M.P. 140°–142° C. (ether/hexane): $[\alpha]_D^{25} = +144.29°$ ($CH_2Cl_2$, c=0.07). Ir ($CHCl_3$): 1720, 3710 $cm^{-1}$. H NMR (200 MHz): δ0.82 (t, J=7.4 Hz, 3H), 0.94 (s, 3H), 1.11 (s, 3H), 1.12 (s, 3H), 1.21–2.34 (m, 16H), 2.60 (dd, J=3.7, 17.6 Hz, 1H), 2.74 (dd, J=5.0, 17.3 Hz, 1H), 4.35 (bs, 1H), 4.59 (bs. 1H), 5.04 (s, 1H), 5.46 (bs, 1H), 5.58 (dd, J=5.9, 8.6 Hz, 1H), 5.97 (d, J=10.0 Hz, 1H). Mass spectrum: M+-$H_2O$ (386) HRMS: Calc. C $C_{24}H_{36}O_5$ 404.2563 os.?? 404.2591. Anal. for $C_{24}H_{36}O_5$: C, 71.26; H, 8.97. Found: C, 70.75; H, 9.13.

A preferable formulation for an oral dosage of the compound of formula I or II in capsule form is presented in Example 21 below:

EXAMPLE 21

| Ingredients | Amount (mg/tablet) |
| --- | --- |
| 1. Compound of formula I or II | 5.0 |
| 2. Lactose Anhydrous | 134.0 |
| 3. Starch 1500 | 20.0 |
| 4. Microcrystalline Cellulose | 40.0 |
| 5. Magnesium Stearate | 1.0 |
| | 200.0 mg. |

Manufacturing Process

A. Mix together 2, 3 and 4.
B. Mill the mixture through a suitable mill.
C. Add 1 in portions to uniformly mix throughout the mixture. the mixture.
D. Mill the mixture.
E. Add 5 through a suitable mill compress mixture into tablet form.

EXAMPLE 22

Preferred Formulation for Topical Dosage of Compounds of Formula I or II.

| | |
| --- | --- |
| 1. Compound of Formula I or II | 10.0 micrograms |
| 2. Stearyl alcohol | 0.04 g |
| 3. Cetyl alcohol | 0.04 g |
| 4. Mineral oil | 0.03 g |
| 5. Polysorbate 60 | 0.04 g |
| 6. Sorbitan stearate | 0.04 g |

-continued

| | |
|---|---|
| 7. Propylene glycol | 0.10 g |
| 8. Methyl paraben | 0.001 g |
| 9. Propyl paraben | |
| 10. Water | q.s. to 1 g |

Manufacturing Process

A. Heat 2 through 6 to 80° C., which melts all ingredients (oil phase).

B. Dissolve 1 in oil phase.

C. Heat 7 and 10 to 90° C. (aqueous phase).

D. Dissolve 8 and 9 in aqueous phase.

E. Add aqueous phase to oil phase, and stir rapidly to form an emulsion.

F. Cool slowly to 50° C. to allow the emulsion to congeal.

G. Continue stirring slowly until the emulsion cools to room temperature.

We claim:

1. A compound of the formula

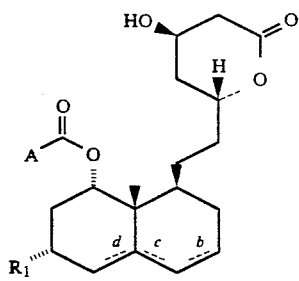

I wherein $R_1$ is hydrogen; and A is

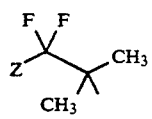

wherein Z is lower alkyl; and b and d are carbon-carbon bonds or c is a carbon-carbon bond.

2. The compound in accordance with claim 1, [4R-[4β,6β,6[8S,(8α,8aβ)]]]-6-[2-[1,2,6,7,8,8a-hexahydro-8)3,3-difluoro-2,2-dimethyl-1-butyryloxy)-8a-methyl-1-naphthalenyl]ethyl]tetrahydro-4-hydroxy-2H-pyran-2-one.

3. A composition for treating hyperproliferative skin disease which comprises a pharmaceutically acceptable carrier and an antihyperproliferatively effective amount of a compound of the formula

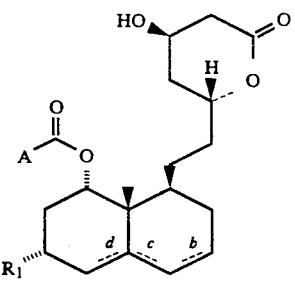

I wherein $R_1$ is hydrogen; and A is

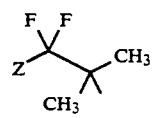

wherein Z is lower alkyl; and b and d are carbon-carbon bonds or c is a carbon-carbon bond.

4. The composition in accordance with claim 3, wherein the compound of formula I is [4R-[4β,6β,6[8S,(8α,8aβ)]]]-6-[2-[1,2,6,7,8,8a-hexahydro-8-)3,3-difluoro-2,2-dimethyl-1-butyryloxy)-8a-methyl-1-naphthalenyl]ethyl]tetrahydro-4-hydroxy-2H-pyran-2-one.

5. A method for treating a hyperproliferative skin disease in a patient in need of such treatment comprising administering an antihyperproliferatively effective amount of a compound of the formula

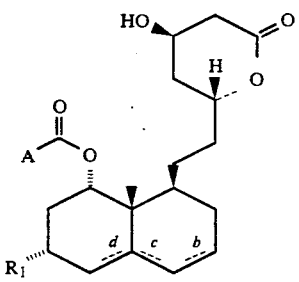

I wherein $R_1$ is hydrogen; and A is

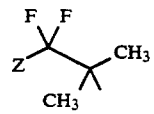

wherein Z is lower alkyl; and b and d are carbon-carbon bonds or c is a carbon-carbon bond.

6. The method in accordance with claim 5 wherein the compound of formula I is administered orally.

7. The method in accordance with claim 5 wherein the compound of formula I is administered topically.

8. The method in accordance with claim 5 wherein the compound of formula I is [4R-[4β,6β,6[8S,(8α,8aβ)]]]-6-[2-[1,2,6,7,8,8a-hexahydro-8-)3,3-difluoro-2,2-dimethyl-1-butyryloxy)-8a-methyl-1-naphthalenyl]ethyl]tetrahydro-4-hydroxy-2H-pyran-2-one.

* * * * *